US008618079B2

(12) United States Patent
Ebetino et al.

(10) Patent No.: US 8,618,079 B2
(45) Date of Patent: Dec. 31, 2013

(54) IMIDAZO[1,2-A] PYRIDINYL BISPHOSPHONATES

(75) Inventors: Frank Hallock Ebetino, Cincinnati, OH (US); Adam Mazur, Cincinnati, OH (US); Mark Walden Lundy, Cincinnati, OH (US); Robert Graham Russell, Oxford (GB)

(73) Assignee: Isis Innovation Limited, Oxford (GB)

( * ) Notice: Subject to any disclaimer, the term of this patent is extended or adjusted under 35 U.S.C. 154(b) by 38 days.

(21) Appl. No.: 13/120,078

(22) PCT Filed: Sep. 22, 2009

(86) PCT No.: PCT/US2009/057817
§ 371 (c)(1),
(2), (4) Date: Jun. 7, 2011

(87) PCT Pub. No.: WO2010/033978
PCT Pub. Date: Mar. 25, 2010

(65) Prior Publication Data
US 2011/0230443 A1      Sep. 22, 2011

Related U.S. Application Data

(60) Provisional application No. 61/098,981, filed on Sep. 22, 2008.

(51) Int. Cl.
*A61K 31/675* (2006.01)
(52) U.S. Cl.
USPC .......................................................... 514/80
(58) Field of Classification Search
None
See application file for complete search history.

(56) References Cited

U.S. PATENT DOCUMENTS 4,990,503 A * 2/1991 Isomura et al. ................ 514/80

FOREIGN PATENT DOCUMENTS

JP 02-48587 * 2/1990 ............ C07F 9/6561
WO 99/02539 1/1999
WO 2008/063865 5/2008

OTHER PUBLICATIONS

STN Search Report (Accession No. 1990:478695).*
Williams et al (Foye's Principles of Medicinal Chemistry, 5th Edition, pp. 59-63, 2002).*
Patani et al (Chem Rev 96:3147-3176, 1996).*
Supplementary European Search Report Application No. 09815377.8—2101/2350076 (PCT/US2009057817) mailed Feb. 13, 2012, 4 pages.
Szabo, C. et al. "An investigation of bone resorption and *Dictyostelium discoideum* Growth Inhibition by Bisphosphonate Drugs" Journal of Medicinal Chemistry. 2002, 45(14), 2894-2903.
Fulfaro, F. et al. "The role of bisphosphonates in the treatment of painful metastatic bone disease: a review of phase III trials" Pain. 1998, vol. 78, pp. 157-169.
Sanders, J. M. et al. "3-D QSAR investigations of the inhibition of Leishmanina major Farnesyl Pyrophophate Synthesis by Bisphosphonates" Journal of Medicinal Chemistry. 2003, 46(24), 5171-5183.
Lecercle, D. et al. "Phosphine-catalyzed alpha-P-addition on activated alkynes: new route to P-C-P backbones" Organic Letters. 2006, 8(19), 4283-4285.
PCT Search Report dated May 7, 2010.

* cited by examiner

*Primary Examiner* — Craig Ricci
(74) *Attorney, Agent, or Firm* — Thomas | Horstemeyer, LLP

(57) ABSTRACT

Novel imidazo[1,2-α]pyridinyl bisphosphonate compounds are disclosed, as well as methods of preparing the compounds, pharmaceutical compositions including the compounds, and administration of the compounds in methods of treating abnormal calcium and phosphate metabolism, including bone and joint diseases and other disorders.

18 Claims, 7 Drawing Sheets

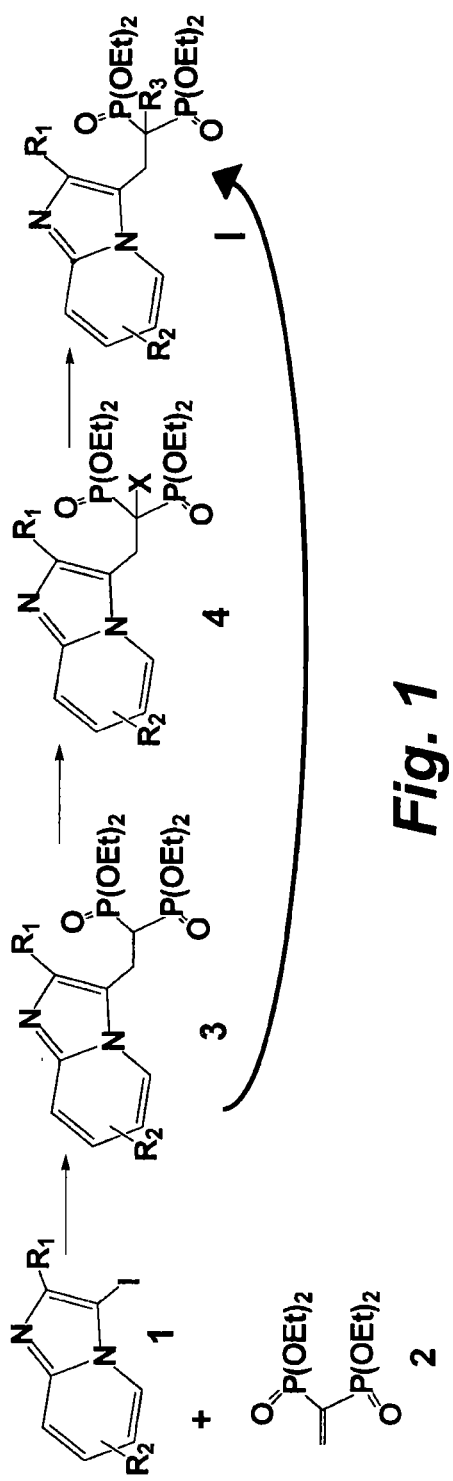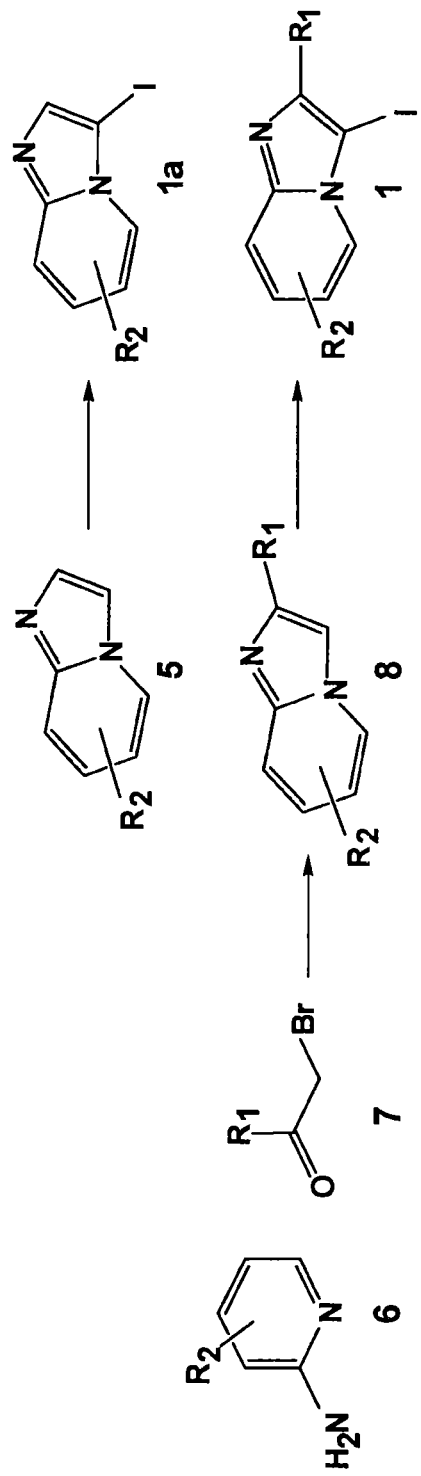
Fig. 1
Fig. 2
R1, R2 = H, lower alkyl, F

IMIDAZO[1,2-A] PYRIDINYL BISPHOSPHONATES

CROSS-REFERENCE TO RELATED APPLICATIONS

This application is the National Stage of International Application no. PCT/US2009/057817 filed Sep. 22, 2009, which claims the benefit of U.S. Provisional Pat. App. Ser. No. 61/098,981, entitled "IMIDAZO[1,2-α]PYRIDINYL BISPHOSPHONATES" filed on Sep. 22, 2008, the contents of which are incorporated by reference as if fully set forth herein.

FIELD OF THE DISCLOSURE

Novel bisphosphonate compounds are disclosed, as well as their activity as anti-resorptive agents and for treatment and prevention of disorders associated with bone metabolism, abnormal calcium and phosphate metabolism, and other disorders. Processes for preparing the novel bisphosphonate compounds, as well as methods of using them and pharmaceutical compositions containing them are also disclosed.

BACKGROUND

Bisphosphonates were first developed to complex calcium in hard water to improve detergent performance. Bisphosphonates have since been found to be useful in the treatment and prevention of diseases or conditions characterized by abnormal calcium and phosphate metabolism. Such conditions may be divided into two broad categories: conditions that are characterized by anomalous mobilization of calcium and phosphate leading to general or specific bone loss or excessively high calcium and phosphate levels in the fluids of the body. Such conditions are sometimes referred to as pathological hard tissue demineralization; and conditions which cause or result from deposition of calcium and phosphate anomalously in the body. These latter conditions are sometimes referred to as pathological calcifications.

The first category includes osteoporosis, a condition in which bone hard tissue is lost disproportionately to the development of new hard tissue ultimately resulting in fractures. Essential quantities of cancellous and cortical bone are lost, and marrow and bone spaces become larger, resulting in reduced bone strength. Bone also becomes less dense and fragile.

Osteoporosis can be sub-classified as genetic, senile, drug-induced (e.g., adrenocorticoid, as can occur in steroid therapy), disease-induced (e.g., arthritic and tumor), etc., however the manifestations are similar. Another condition in the first category is Paget's disease (osteitis deformans). In this disease, dissolution of normal bone occurs, which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastasis are conditions also included in the first category. The second category, involving conditions manifested by anomalous calcium and phosphate deposition, includes myositis ossificans progressiva, calcinosis universalis, and such afflictions as arthritis, neuritis, bursitis, tendonitis, and other inflammatory conditions which predispose involved tissue to deposition of calcium phosphates.

A variety of polyphosphonic acid derivatives have been proposed for use in the treatment and prophylaxis of conditions involving abnormal calcium and phosphate metabolism. For example diphosphonates, like ethane-1-hydroxy-1,1-diphosphonic acid (EHDP), propane-3-amino-1-hydroxy-1,1-diphosphonic acid (APD), and dichloromethane diphosphonic acid ($Cl_2MDP$) have been the subject of considerable research efforts in this area. Paget's disease and heterotopic ossification have been treated with EHDP. Similarly, risedronate and alendronate have been used for treatment of bone disorders, and U.S. Pat. No. 4,990,503 discloses heterocyclic bisphosphonic acid derivatives and their use as bone resorption inhibitors.

Bisphosphonates tend to inhibit the resorption of bone tissue, which is beneficial to patients suffering from excessive bone loss. However, many of the early bisphosphonates, such as EHDP, APD, and $Cl_2MDP$, have a greater propensity of inhibiting bone mineralization at high doses, a phenomenon which is particularly problematic during the course of long term treatment. Bone mineralization is essential for treatment of disorders such as osteoporosis. Bone tissue that is not adequately mineralized is soft and flexible and does not contribute to bone strength or skeletal support. Accordingly, long-term inhibition of mineralization could result in harmful side effects, such as increased risk of fracture, rickets in children and osteomalacia in adults. Even with the development of more potent bisphosphonates, which allows for administration of smaller dosages, there is still a potential for bone mineralization defects.

Farnesyl pyrophosphate synthase (FPPS) is a key regulatory enzyme in the mevalonate pathway. This pathway, ubiquitous in mammalian cells, provides essential lipid molecules, such as cholesterol and isoprenoids, with the latter necessary for posttranslational prenylation of small GTPases. The blockage of this pathway is a concept that has found widespread clinical use, with statins as drugs that inhibit hydroxymethylglutaryl CoA reductase and reduce cholesterol biosynthesis, and nitrogen-containing bisphosphonates (N-BPs) as drugs for osteoporosis therapy that target FPPS and inhibit protein prenylation. In the case of N-BPs, the unique bone-targeting pharmacokinetic properties of these compounds cause selected inhibition of FPPS and loss of prenylated proteins in osteoclasts, thereby inhibiting the bone-destroying function of these cells.

SUMMARY

The imidazo[1,2-α]pyridinyl bisphosphonate derivatives described herein are useful in the treatment and/or prevention of disorders associated with abnormal calcium and phosphate metabolism, including bone and joint diseases, such as osteoporosis, rheumatoid arthritis, osteoarthritis, Paget's disease, alveolar bone loss often associated with periodontal disease and bone-related cancer therapy. The compounds described herein have the ability to inhibit the resorption of bone tissue and are inhibitors of farnesyl pyrophosphate synthase (FPPS). Furthermore, such compounds correspondingly have orthopedic uses (including, but not restricted to, fracture repair and implant fixation; and prevention of prosthesis loosening, and osteonecrosis of various bones). Other uses include immunomodulation and anti-inflammatory effects, and use in various parasitic disorders (eg. malaria, leishmaniasis, trypanasomal diseases, entamoeba, giardia, and cryptosporidial infections).

One aspect of the present disclosure, therefore, encompasses compounds, or pharmaceutically acceptable salts thereof, where the compound has a structure according to the general formula I

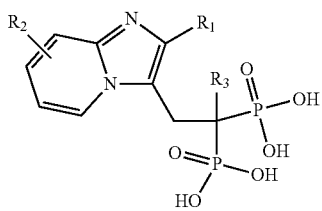

where $R_1$ is hydrogen, hydroxyl, lower alkyl, methoxy, or F; $R_2$ is hydrogen, hydroxyl, lower alkyl, or F; and $R_3$ is F, Cl, or hydrogen.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

Embodiments of this aspect of the disclosure can be, but are not limited to, compounds selected from the group consisting of: 1-fluoro-2-(imidazo[1,2-α]pyridin-3-yl-ethyl-bisphosphonic acid; 2-(imidazo[1,2-α]pyridin-3-yl)ethyl-bisphosphonic acid; 2-(6-methylimidazo[1,2-α]pyridin-3-yl)-ethyl-bisphosphonic acid; [(2-ethyl-imidazo[1,2-α]pyridin-3-yl)methyl]-bisphosphonic acid; 2-(2-t-butylimidazo[1,2-α]pyridin-3-yl)ethane-1,1- bisphosphonic acid; 2-(7-methylimidazo[1,2-α]pyridin-3-yl)-ethyl-bisphosphonic acid; [2-(8-hydroxy-imidazo[1,2-α]pyridin-3-yl)-1-ethane]-bisphosphonic acid; 2-(6-fluoroimidazo[1,2-α]pyridin-3-yl) ethyl-bisphosphonic acid; and 1-fluoro-2-(7-methylimidazo[1,2-α]pyridin-3-yl)-ethyl-bisphosphonic acid.

In one embodiment of this aspect of the disclosure, the compound is 1-fluoro-2-(imidazo[1,2-α]pyridin-3-yl)-ethyl-bisphosphonic acid, or a pharmaceutically acceptable salt thereof.

Another aspect of the disclosure encompasses pharmaceutical compositions that comprise a compound, or a pharmaceutically acceptable salt thereof, wherein the compound has a structure according to Formula I

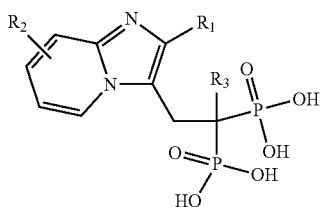

where $R_1$ is hydrogen, hydroxyl, lower alkyl, methoxy, or F; $R_2$ is hydrogen, hydroxyl, lower alkyl, or F; and $R_3$ is F, Cl, or hydrogen, and a pharmaceutically acceptable carrier.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

Embodiments of this aspect of the disclosure can be, but are not limited to, compounds selected from the group consisting of: 1-fluoro-2-(imidazo[1,2-α]pyridin-3-yl-ethyl-bisphosphonic acid; 2-(imidazo[1,2-α]pyridin-3-yl)ethyl-bisphosphonic acid; 2-(6-methylimidazo[1,2-α]pyridin-3-yl)-ethyl-bisphosphonic acid; [(2-ethyl-imidazo[1,2-α]pyridin-3-yl)methyl]-bisphosphonic acid; 2-(2-t-butylimidazo[1,2-α]pyridin-3-yl)ethane-1,1- bisphosphonic acid; 2-(7-methylimidazo[1,2-α]pyridin-3-yl)-ethyl-bisphosphonic acid; [2-(8-hydroxy-imidazo[1,2-α]pyridin-3-yl)-1-ethane]-bisphosphonic acid; 2-(6-fluoroimidazo[1,2-α]pyridin-3-yl) ethyl-bisphosphonic acid; and 1-fluoro-2-(7-methylimidazo[1,2-α]pyridin-3-yl)-ethyl-bisphosphonic acid.

In one embodiment of this aspect of the disclosure, the composition comprises 1-fluoro-2-(imidazo[1,2-α]pyridin-3-yl)-ethyl-bisphosphonic acid, or a pharmaceutically acceptable salt thereof, and a pharmaceutically acceptable carrier.

Yet another aspect of the disclosure encompasses methods of modulating calcium or phosphate metabolism in a subject animal or human, the method comprising administering to the subject animal or human an effective amount of a compound, or pharmaceutically acceptable salt thereof, where the compound has a structure according to Formula I

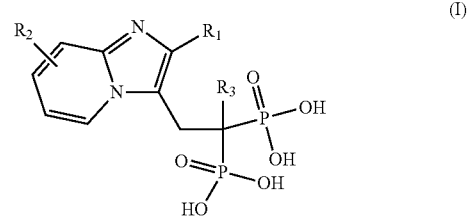

where $R_1$ is hydrogen, hydroxyl, lower alkyl, methoxy, or F; $R_2$ is hydrogen, hydroxyl, lower alkyl, or F; and $R_3$ is F, Cl, or hydrogen, whereupon the calcium or phosphate metabolism in the subject animal or human is modified.

In embodiments of the methods of this aspect of the disclosure, the calcium or phosphate metabolism in the subject animal or human before administering the compound thereto can be abnormal and associated with a skeletal disorder. In some embodiments of this aspect of the disclosure, the skeletal disorder can be selected from the group consisting of, but is not limited to, osteoporosis, rheumatoid arthritis, osteoarthritis, Paget's disease, alveolar bone loss, a bone-related cancer, and an orthopedic disorder.

In other embodiments, the disorder may be a non-skeletal disorder such as, but not limited to, a non-bone cancer, an immunomodulatory disorder, an inflammatory disorder, or a parasitic disorder. In these embodiments, the parasitic disorder can be, but is not limited to, malaria, leishmaniasis, a trypanasomal disease, an entamoebal infection, a giardia infection, and a cryptosporidial infection.

In the embodiments of the methods of this aspect of the disclosure, the compound administered to the subject animal or human can modify the activity of farnesyl pyrophosphate synthase in the subject animal or human.

In the embodiments of the methods of this aspect of the disclosure, the compound, or pharmaceutically acceptable salt thereof, or is selected from the group consisting of: 1-fluoro-2-(imidazo[1,2-α]pyridin-3-yl-ethyl-bisphosphonic acid; 2-(imidazo[1,2-α]pyridin-3-yl)-ethyl-bisphosphonic acid; 2-(6-methylimidazo[1,2-α]pyridin-3-yl)ethyl-bisphosphonic acid; [(2-ethyl-imidazo[1,2-α]pyridin-3-yl)-methyl]-bisphosphonic acid; 2-(2-t-butylimidazo[1,2-α]pyridin-3-yl)ethane-1,1-bisphosphonic acid; 2-(7-methylimidazo[1,2-α]pyridin-3-yl)ethyl-bisphosphonic acid; [2-(8-hydroxy-imidazo[1,2-α]pyridin-3-yl)-1-ethane]-bisphosphonic acid; 2-(6-fluoroimidazo[1,2-α]pyridin-3-yl)-ethyl-bisphosphonic acid; and 1-fluoro-2-(7-methylimidazo[1,2-α]pyridin-3-yl)-ethyl-bisphosphonic acid.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1 schematically illustrates Scheme 1 as a process for making compounds of Formula I.

FIG. 2 schematically illustrates a process for making compound I, used in the synthesis of compounds of Formula I.

Figure 3:
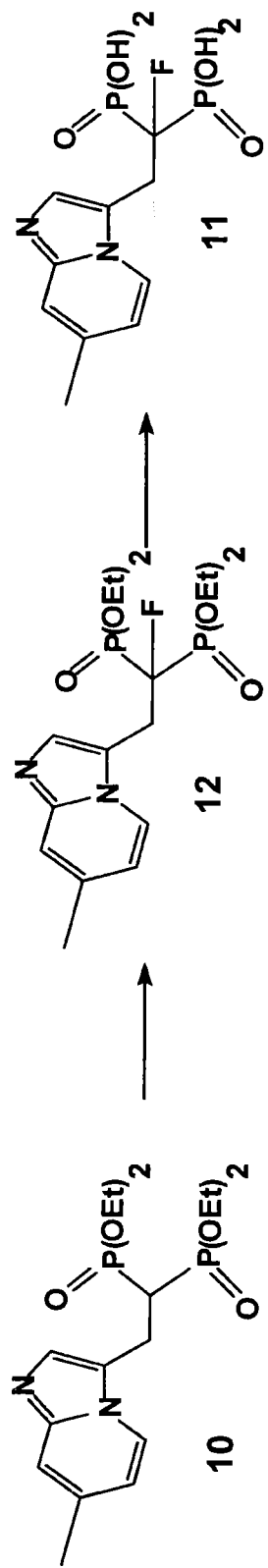
FIG. 3 schematically illustrates a process for making 1-fluoro-2-(7-methyl)-imidazo-[1,2-α]pyridin-3-yl-ethyl-bisphosphonic acid.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean " includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Abbreviations

EHDP, ethane-1-hydroxy-1,1-diphosphonic acid; APD, propane-3-amino-1-hydroxy-1,1-diphosphonic acid; Cl$_2$MDP dichloromethane diphosphonic acid; FPPS, farnesyl pyrophosphate synthase; N-BP, nitrogen-containing bisphosphonate Definitions The term "lower alkyl" as used herein refers to a linear or branched, saturated hydrocarbon having from 1 to 4 carbon atoms. Representative ($C_1$-$C_4$)-alkyl groups include, but are not limited to, methyl, ethyl, propyl, isopropyl, butyl, sec-butyl, and tert-butyl. Similarly, "($C_1$-$C_4$)-alkyl" as used herein refers to a linear or branched, saturated hydrocarbon, optionally substituted as described above, having from 1 to 4 carbon atoms. The carbon number, as used herein, refers to the carbon backbone and carbon branching, but does not include carbon atoms of the substituents, such as alkoxy substitutions and the like.

The terms "administer", "administering", or "administration", as used herein refer to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of the compound within the animal's body.

The term "subject" as used herein includes, without limitation, a human, mouse, rat, guinea pig, dog, cat, horse, cow, pig, monkey, chimpanzee, baboon, or rhesus monkey. In one embodiment, the animal is a mammal.

The term "conditions effective to" as used herein refers to synthetic reaction conditions that will be apparent to those skilled in the art of synthetic organic chemistry.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "pharmaceutically acceptable salt", as used herein, refers to salts derived from organic and inorganic acids of a compound described herein. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound described herein having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH-($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes hydrates of a compound described herein.

The term "pharmaceutically acceptable carrier" as used herein refers to a diluent, adjuvant, excipient, or vehicle with which a heterodimeric probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the heterodimeric probes and pharmaceutically acceptable carriers preferably should be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "physiologically acceptable" as used herein refers to a composition that, in contact with a cell, isolated from a natural source or in culture, or a tissue of a host, has no toxic effect on the cell or tissue.

Compounds

The compounds described herein demonstrate reduced mineral affinity compared to many known bisphosphonate compounds currently used for treatment of osteoporosis and other bone disorders (e.g., minodronate, risedronate, alendronate, zoledronate, ibandronate). The presence of fluorine, chlorine, or hydrogen at the phosphonate-bearing carbon atom (i.e., $R_3$ in the compounds described herein) is believed to result in reduced mineral affinity. In known bisphosphonate compounds, this carbon atom bears an hydroxyl moiety which together with the two phosphonate moieties is thought to help create a high affinity for bone mineral. Previous studies demonstrated that, in other classes of bisphosphonates, such as pyridyl alkyl bisphosphonates and the gem phosphono-carboxylate analogs of bisphosphonates, replacement of the hydroxyl moiety with such moieties reduces the affinity for bone mineral and can reduce affinity for the FPPS enzymatic target site (e.g., halogen or hydrogen) and significantly lowers cellular potency. (Marma et al., *J. Med. Chem.*, 50: 5967-5975.)

The pyridylimidazoylalkyl bisphosphonate compounds described herein, however, demonstrate a high degree of cellular potency, despite the substitution at the carbon atom adjacent to the phosphonate groups, and the accompanying reduction in mineral affinity. This result is unexpected, as the reduction in mineral affinity is expected to lead to a marked reduction in in vivo potency. Moreover, the greater cellular potency (FPPS enzyme inhibition) provides a more potent anti-resorptive effect in vivo than many previous bisphosphonate compounds.

The reduced mineral affinity of the bisphosphonate compounds described herein offers greater control of dosing, as the compound's effects on bone metabolism will dissipate faster than with traditional bisphosphonate compounds having higher mineral affinity. The reduced mineral affinity also provides faster release from bone and may offer greater utility to younger patients, patients of childbearing age, and for those that may require combination or sequential dosing of other bone therapeutic agents, particularly in comparison to known bisphosphonate compounds that are currently approved for use in treating bone disorders. It is believed that these lower mineral affinity properties may also offer more even distribution across the multiple bone types and sites in the skeleton. Alternatively, these features may provide improved effects at nearby cells that are less accessible by higher affinity analogs.

Faster release from the bone, subsequent to dosing, allows more flexible use of the bisphosphonate compounds described herein, compared to bisphosphonate compounds known in the art. For example, in some embodiments, the compound described herein can be used for defined periods of time that will allow discontinuation of therapy for contraindicative activities or subsequent use of alternative or additional drugs. For example, anabolic therapies that may be rendered less active when bone turnover is reduced. Similarly, the lower bone affinity offered by the compounds described herein results in less overall skeletal uptake, less overall reduction of bone turnover, and less effect on skeletal modeling/remodeling, thus leaving the regenerative processes of bone functioning more normally. This may result in a better quality of bone as more normal bone turnover is maintained while the typical anti-fracture benefits of bisphosphonate drugs are delivered. As a result, treatment is available to younger patients who might want to avoid the effects of traditional bisphosphonates (e.g., reduction in bone turnover and accompanying deleterious effects) over longer periods of time. Moreover, it is anticipated that the compounds described herein provide anti-resorptive or fracture benefits while maintaining better bone quality, in contrast to high mineral affinity analogs that induce less physiological and extreme bone turnover reduction.

Other advantages of the low mineral affinity of the compounds described herein include a higher propensity for interacting deep within bone tissue and thus offering beneficial effects of bisphosphonates to osteocytes deep within the bone. In addition, lower mineral affinity compounds are more likely to produce higher concentrations in synovial fluid, as well as higher extracellular levels of bisphosphonate compound (e.g., around osteoclasts, macrophages, chondrocytes, and tumor cells), facilitating more effective daily, weekly or monthly administration. The compounds described herein exhibit lower total skeletal turnover reduction, as well as a more defined therapy as a result of faster release after ceasing therapy. This feature may therefore offer additional benefits during the treatment of multiple conditions associated with bone loss such as bone erosions associated with arthritic joints and tumor initiation and growth associated with bone metastasis.

In one embodiment, the bisphosphonate compounds described herein are administered as an adjuvant with one or more anti-inflammatory or immunomodulatory compounds. The use of higher affinity bisphosphonate compounds known in the art with anti-inflammatory compounds is limited due to toxicity issues related to the combination of these compounds. In particular, higher dosages of anti-inflammatory compounds are required to protect bone, when co-administered with known bisphosphonate compounds. Because of the higher dosages, however, side effects and other toxicity-related effects are quickly observed and the co-administration must be stopped. Because the compounds described herein have a lower affinity for bone, however, they can be used effectively to protect bone in combination with anti-inflammatory or immunomodulatory agents at dosage levels that are low enough to not trigger toxic effects. Accordingly, the compounds described herein provide improved protection against bone erosion, while at the same time offering improved joint preservation, while inducing less overall skeletal turnover reduction than traditional bisphosphonates. In one embodiment, the compounds described herein are useful for inhibiting bone erosion. In another embodiment, the compounds described herein are useful for inhibiting both inflammation and bone erosion. For example, such anti-inflammatory, immunomodulatory and anti-erosion properties are achieved in some embodiments when the bisphosphonate compounds described herein are co-administered with an anti-inflammatory or immunomodulatory agent. In these embodiments, the anti-inflammatory or immunomodulatory agent can be administered at lower doses than it would be when administered on its own. Thus, in some embodiments, the bisphosphonate compound is administered in combination or in sequence with the one or more anti-inflammatory or immunomodulatory compounds. Exemplary anti-inflammatory or immunomodulatory compounds include, without limitation, biologic anti-inflammatory or immunomodulatory compounds such as tumor necrosis factor antagonists, NSAIDs, glucocorticoids and methotrexate.

The synergy between the bisphosphonate compounds described herein is also beneficial for treatment of osteoarthritis. In osteoarthritis, the afflicted joints are known to exhibit higher bone turnover. Treatment with a combination of one or more of the bisphosphonate compounds described herein and an anti-inflammatory or immunomodulatory compound can normalize the turnover at these sites without producing excessive bone turnover in the remaining skeleton. In addition, the co-administration maximizes any potential anti-apoptotic effects on chondrocytes that are delivered to this joint by the virtue of these lower affinity bisphosphonate analogs. The compounds described herein are useful for improvement of joint function.

Similarly, the compounds described herein can also be co-administered with anabolic compounds. With bisphosphonate compounds known in the art, a wash out phase is necessary when treating patients who have been previously administered anabolic compounds, such as parathyroid hormone and prostaglandins. The lower bone affinity of the compounds described herein, however, results in less interference with these anabolic agents. Accordingly, the compounds described herein can be administered to patients treated with anabolic agents with little or no washout period. In one embodiment, the compounds described herein are co-administered with one or more anabolic compounds. One exemplary anabolic compound is a compound based on parathyroid hormones (PTH) such as PTH 1-34 (FORTEO®). Anabolic therapy is often prescribed to patients with very serious osteoporotic disease and/or those who do not respond to bisphosphonate therapy. Accordingly, the bisphosphonate compounds described herein are useful for treatment of osteoporotic disease, as well as subjects who respond poorly to bisphosphonate therapy.

Synthesis Procedures

The compounds and pharmaceutically acceptable salts described herein can be prepared using a variety of methods starting from commercially available compounds, known compounds, or compounds prepared by known methods. General synthetic routes to many of the compounds described herein are included in the following schemes. It is understood by those skilled in the art that protection and deprotection steps not shown in the Schemes may be required for these syntheses, and that the order of steps may be changed to accommodate functionality in the target molecule. The need for protection and deprotection, and the selection of appropriate protecting groups can be found, for example, in Greene and Wuts, *Protecting Groups in Organic Synthesis*, Second Edition, John Wiley & Sons (1991), which is incorporated by reference in its entirety.

In the schemes described herein, appropriate polar solvents include, but are not limited to, dimethyl sulfoxide, dimethylformamide, tetrahydrofuran, methanol and ethanol. Suitable acid binding agents include, but are not limited to, organic tertiary bases, such as, for example, triethylamine, triethanolamine, 1,8-diazabicyclo[5.4.0]undec-7-ene (DBU), and diisopropylethylamine (DIPEA); and alkaline metal carbonates, such as, for example, potassium carbonate and sodium carbonates. Suitable reducing agents include, but are not limited to, sodium cyanoborohydride and sodium triacetoxyborohydride.

Scheme 1, as shown in FIG. 1, illustrates one process for making compounds of Formula I, where $R_1$, $R_2$, and $R_3$ are as defined herein. As shown in Scheme I, to prepare compounds of Formula I, compound 1, containing a leaving group, such as iodine, is reacted with vinyl phosphonate 2 under conditions effective to produce compound 3. For example, in some embodiments, the reaction is performed in the presence of n-BuLi at a reduced temperature, e.g., −78° C. When $R_3$ is other than hydrogen (i.e., F or Cl), compound 3 is reacted with a halogenating compound, e.g., SELECTFLUOR® (Air Products, Inc.), sodium hypochlorite (reacted with free acid) under catalytic conditions, for example in the presence of an appropriate amount of a catalytic reagent, e.g., 18-crown-6, to produce compound 4. The reaction is carried out in appropriate solvents, e.g., potassium hydride and tetrahydrofuran at reduced temperature, e.g. 0° C. Depending on the identity of $R_3$, compound 3 (where $R_3$ is hydrogen) or compound 4 (where $R_3$ is other than hydrogen) is reacted under conditions effective to convert the ethoxy groups to hydroxy groups, thereby producing a compound of Formula I. It is further contemplated that in some embodiments of the compounds of the disclosure, $R_3$ may not be —OH.

In some embodiments, the reaction is carried out in the presence of trimethyl silylbromide.

Scheme 2, as shown in FIG. 2, illustrates one process for making one of the starting materials for Scheme 1, compound 1. Where $R_1$ is other than hydrogen, an aminopyridine compound (compound 6) is reacted with a halogenated ketone compound (compound 7) under conditions effective to produce the pyridylimidazoyl compound 8. In some embodiments, the reaction is carried out in the presence of sodium carbonate and ethanol at elevated temperature, e.g., 70° C. Compound 1, or, when $R_1$ is hydrogen, compound 1a, is produced by reacting compound 8 (or compound 5, where $R_1$ is hydrogen) under conditions effective to produce a compound of Formula I. In some embodiments, the reaction is performed in the presence of N-iodosuccimide and acetonitrile.

The compounds and pharmaceutically acceptable salts of the compounds described herein are also useful in the manufacture of medicaments for treating or preventing disorder associated with abnormal calcium and phosphate metabolism in a mammal.

Pharmaceutical Compositions

Therapeutic compounds as described herein can be incorporated into pharmaceutical compositions. Such compositions typically include the active ingredient and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers can include, but are not limited to, physiological saline, bacteriostatic water, or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from pressured container or dispenser which contains a suitable propellant, e.g., a gas such as carbon dioxide, or a nebulizer. Such methods include those described in U.S. Pat. No. 6,468,798. Compositions for inhalation can also include propellants, surfactants, and other additives, e.g., to improve dispersion, flow, and bioavailability.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Pharmaceutically acceptable compositions of the present disclosure, therefore, may comprise a pharmaceutically-acceptable excipient. The term "pharmaceutically-acceptable excipient," as used herein, means any physiologically inert, pharmacologically inactive material known to one skilled in the art, which is compatible with the physical and chemical characteristics of the isomer herein. Pharmaceutically-acceptable excipients include, but are not limited to, polymers, resins, plasticizers, fillers, lubricants, diluents, binders, disintegrants, solvents, co-solvents, surfactants, preservatives, sweetening agents, flavoring agents, pharmaceutical-grade dyes or pigments, and viscosity agents.

Flavoring agents and dyes and pigments among those useful herein include those described in Handbook of Pharmaceutical Excipients (4$^{th}$ ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorobutanol, benzyl alcohol, thimerosal, phenylmercuric acetate and nitrate, nitromersol, benzoalkonium chloride, cetylypridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, ethylcellulose, cellulose acetate trimellitate, hydroxypropylmethylcellulose phthalate, cellulose acetate phthalate, polyvinyl acetate phthalate.

Suitable lubricants include, but are not limited to, magnesium stearate, stearic acid, and talc.

The pharmaceutical compositions described herein, in some embodiments, optionally may comprise a chelating agent. The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms.

The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is formed, each successive donor atom that binds creates a ring containing the metal atom. A chelating agent may be bidentate, tridentate, tetradentate, etc., depending upon whether it contains two, three, four, or more donor atoms capable of binding to the metal atom. See Kirk-Othmer Encyclopedia of Chemical Technology (4$^{th}$ ed. 2001).

Chelating agents suitable for use in the compositions described herein include any pharmaceutically-acceptable chelating agent. Non-limiting examples of chelating agents suitable for use in the present disclosure include EDTA, citric acid, malic acid, tartaric acid, lactic acid, aspartic acid, glutamic acid, lysine, sodium hexametaphosphate, and combinations thereof.

A monodentate complexing agent may be used in place of a polydentate chelating agent. Suitable monodentate complexing agents include, but are not limited to, phosphates (e.g., sodium phosphate, sodium aluminum phosphate, sodium acid phosphate, dipotassium phosphate, disodium phosphate, monobasic) and carboxylic acids (e.g., fumaric acid, acetic acid). In one embodiment, the monodentate complexing agent is acetic acid.

The amount of chelating agent present in the oral dosage form of the present disclosure will depend on the particular chelating agent selected and the amount of bisphosphonate compound present in the oral dosage form. Generally, the oral dosage forms of the present disclosure will contain a safe and effective amount of a chelating agent suitable for achieving the desired chelating effect. In one embodiment, the oral dosage form contains from about 10 mg to about 1000 mg of a chelating agent per unit dose. In another embodiment, the oral dosage forms contain from about 10 mg to about 500 mg of a chelating agent per unit dose. When the chelating agent is EDTA, the preferred range is from about 10 mg to about 500 mg, preferably from about 25 mg to about 250 mg per unit dose. When the chelating agent is citric acid or any other chelating agent, the preferred range is from about 25 mg to about 1000 mg, preferably from about 50 mg to about 500 mg per unit dose.

Such pharmaceutical compositions are prepared, for example, using a method including admixing the compound or pharmaceutically acceptable salt of the compound and a pharmaceutically acceptable excipient. Admixing is accomplished using methods well known for admixing a compound or a pharmaceutically acceptable salt of a compound and a physiologically acceptable excipient. Examples of such excipients are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable excipients include are those that are compatible with the other ingredients in the formulation and biologically acceptable.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule.

The compounds or pharmaceutically acceptable salts of the compounds described herein may be administered orally or parenterally, neat or in combination with conventional pharmaceutical carriers as described above. The compounds or pharmaceutically acceptable salts of the compounds described herein can also be administered by any convenient route, for example, orally, by infusion or bolus injection, by absorption through epithelial or mucocutaneous linings (e.g., oral, rectal, vaginal, and intestinal mucosa, etc.) and can be administered together with another therapeutic agent.

It is understood that the dosage, regimen and mode of administration of these compounds will vary according to the malady and the individual being treated and will be subject to the judgment of the medical practitioner involved. In some embodiments, administration of one or more of the compounds or pharmaceutically acceptable salts of the compounds described herein begins at a low dose and is increased until the desired effects are achieved.

The amount of the compound or a pharmaceutically acceptable salt of the compound delivered is an amount that is effective for treating or preventing bone metabolism disorder. In addition, in vitro or in vivo assays are optionally employed to help identify optimal dosage ranges. The precise dose to be employed will also depend on the route of administration, the condition, the seriousness of the condition being treated, as well as various physical factors related to the individual being treated, and should be decided according to the judgment of a health-care practitioner. The number and frequency of dosages corresponding to a completed course of therapy will be determined according to the judgment of a health-care practitioner.

The amount of the compound or a pharmaceutically acceptable salt of the compound that is effective for treating or preventing a bone disorder will typically range from about 0.01 mg/kg to about 1 g/kg of body weight per day, in one embodiment, from about 1 mg/kg to about 600 mg/kg body weight per day, in one embodiment, from about 1 mg/kg to about 250 mg/kg body weight per day, in another embodiment, from about 10 mg/kg to about 400 mg/kg body weight per day, in another embodiment, from about 10 mg/kg to about 200 mg/kg of body weight per day, in another embodiment, from about 10 mg/kg to about 100 mg/kg of body weight per day, in one embodiment, from about 10 mg/kg to about 25 mg/kg body weight per day, in another embodiment, from about 1 mg/kg to about 10 mg/kg body weight per day, in another embodiment, from about 0.001 mg/kg to about 100 mg/kg of body weight per day, in another embodiment, from about 0.001 mg/kg to about 10 mg/kg of body weight per day, and in another embodiment, from about 0.001 mg/kg to about 1 mg/kg of body weight per day.

A pharmaceutical composition according to the disclsoure can be in unit dosage form. In such form, the composition is sub-divided in unit dose containing appropriate quantities of the compound or pharmaceutically acceptable salt of the compound; the unit dosage form can be packaged compositions, for example, packeted powders, vials, ampoules, pre-filled syringes or sachets containing liquids. The unit dosage form can be, for example, a capsule or tablet itself, or it can be the appropriate number of any such compositions in package form. Such unit dosage form may contain from about 0.01 mg/kg to about 250 mg/kg, in one embodiment from about 1 mg/kg to about 250 mg/kg, in another embodiment from about 10 mg/kg to about 25 mg/kg, and may be given in a single dose or in two or more divided doses. Variations in the dosage will necessarily occur depending upon the species, weight and condition of the patient being treated and the patient's individual response to the medicament.

In one embodiment, the unit dosage form is about 0.01 to about 1000 mg. In another embodiment, the unit dosage form is about 0.01 to about 500 mg; in another embodiment, the unit dosage form is about 0.01 to about 250 mg; in another embodiment, the unit dosage form is about 0.01 to about 100 mg; in another embodiment, the unit dosage form is about 0.01 to about 50 mg; in another embodiment, the unit dosage form is about 0.01 to about 25 mg; in another embodiment, the unit dosage form is about 0.01 to about 10 mg; in another embodiment, the unit dosage form is about 0.01 to about 5 mg; and in another embodiment, the unit dosage form is about 0.01 to about 10 mg.

Any enteric coating which is insoluble at a pH below 5.5 (i.e., that generally found in the mouth, pharynx, esophagus, and stomach), but soluble at pH 5.5 or higher (i.e., that present in the small intestine and the large intestine) can be used in the practice of the present disclosure. Accordingly, when it is desired to effect delivery of the bisphosphonate and the chelating agent to the small intestine, any enteric coating is suitable which is wholly- or partially-insoluble at a pH below 5.5 and soluble at a pH 5.5 or above.

The enteric coating must be applied to the compressed tablet, the capsule (e.g., gelatin, starch, or hydroxypropylmethylcellulose) and/or the beads, particles or granules of active ingredient in a sufficient thickness so that the entire coating does not dissolve in gastrointestinal fluids at a pH below 5.5, but does dissolve at a pH of 5.5 or above. The dissolution or disintegration of the excipient coating generally does not occur until the entry of the coated dosage form into the small intestine.

It is expected that any anionic polymer exhibiting the requisite pH-dependent solubility profile can be used as an enteric coating in the practice of the present disclosure to achieve delivery of the bisphosphonate and chelating agent to the lower GI tract. The coating chosen must be compatible with the particular bisphosphonate active ingredient selected. The preferred polymers for use in the present disclosure are anionic carboxylic polymers. It is particularly preferred that the polymers are acrylic polymers, more preferably partly methyl-esterified methacrylic acid polymers, in which the ratio of free anionic carboxyl groups to ester groups is about 1:1.

The coating can, and usually will, contain a plasticizer and possibly other coating excipients such as coloring agents, surfactant, talc, and/or magnesium stearate, many of which are well known in the coating art. In particular, anionic carboxylic acrylic polymers usually will contain 10-25% by weight of a plasticizer, especially triethyl citrate, tributyl citrate, acteyltriethyl citrate, dibutyl phthalate, diethyl phthalate, polyethylene glycol, acetylated monoglycerides propylene glycol, and triacetin. Conventional coating techniques such as fluid-bed or pan coating are employed to apply the coating. Coating thickness must be sufficient to ensure that the oral dosage form remains essentially intact until the desired site of delivery in the lower GI tract is reached.

The solid oral dosage form may be in the form of a coated compressed tablet which contains particles or granules of the bisphosphonate active ingredient and the chelating agent, or of a soft or hard capsule (e.g., gelatin, starch, or hydroxypropylmethylcellulose), coated or uncoated, which contains beads or particles of the bisphosphonate active ingredient and the chelating agent, which themselves are enterically coated.

For sustained release of the bisphosphonate and chelating agent a sustained release polymer is required to control the dissolution rate of the bisphosphonate and chelating agent from the dosage form. If the bisphosphonate and chelating agent are both soluble (defined as 33 mg/ml or greater in water) then high levels of sustained release polymers are required. Sustained release polymers include but are not limited to hydroxypropylmethylcellulose, hydroxypropylcellulose and Carbomer.

Methods of Use

The present disclosure further relates to a method of treating, preventing or ameliorating disorders of bone metabolism, such as those characterized by abnormal calcium and phosphate metabolism. These methods include the step of administering to a human or other mammal in need thereof a safe and effective amount of a pharmaceutical composition delivered to said human or other mammal via the oral dosage forms described herein.

Diseases characterized by abnormal calcium and phosphate metabolism include, but are not limited to, osteoporosis, secondary osteoporosis, secondary osteoporosis stemming from osteoporosis, osteoarthritis, Paget's disease (osteitis deformans), hyperparathyroidism, hypercalcemia of malignancy, osteolytic bone metastasis, myositis ossificans progressiva, calcinosis universalis, and such afflictions as arthritis, neuritis, bursitis, tendonitis, bone pain, and other inflammatory conditions which predispose involved tissue to loss or deposition of calcium phosphates. The compounds described herein are also useful for other bone disorders and conditions such as, without limitation, fracture repair, prosthesis integration, and osteonecrosis (e.g., of hip or knee). The compounds described herein are also useful for the prevention and treatment of skeletal related events associated with cancer such as metastasis, tumor growth, bone pain, fractures, and such afflictions as arthritis (including bone disease and joint function in osteoarthritis). Further, the compounds described herein are also useful for treatment and prevention of additional skeletal related events induced during the treatment of cancer, such as hormone ablation therapy, aromatase inhibitor therapy, and androgen ablation therapy, particularly in patients suffering from breast or prostate cancer.

The compounds described herein are also useful for the prevention and treatment of parasitic disorders such as malaria and Chagas disease, and disorders of the gastrointestinal tract such as intestinal parasites, and irritable bowel disease. In some embodiments, the compounds described herein are, in some embodiments, useful to inhibit or treat parasitic infections, such as protozoan infections and diseases including malaria, leishmaniasis, trypanasomal diseases, entamoeba, giardia, and cryptosporidial infections.

In some embodiments, the compounds described herein are useful for treating or preventing inflammation disorders. Such disorders include, without limitation, rheumatoid arthritis, and irritable bowel disease. In some embodiments, when used for treating or preventing inflammation disorders, the compounds described herein may be used in combination with one or more anti-inflammatory compounds.

In some embodiments, the compounds described herein are useful for treating, preventing or ameliorating dental disorders. Exemplary disorders include, without limitation, cavities and periodontal disease. In some embodiments, the compounds described herein are useful for treatment related to dental surgical procedures, such as tooth implantation.

In some embodiments, the compounds described herein are useful for treatment related to orthopedic joint implants, for example to improve fixation of artificial joints, or to prevent loosening of implanted joints. In further embodiments, the compounds described herein have orthopedic uses, such as to promote or facilitate fracture repair and bone regeneration, either when used as a sole therapy on in conjunction with other pharmaceutical or non-pharmaceutical orthopedic therapy.

In further embodiments, the compounds described herein offer orthopedic utility in the outcomes of hip, knees or other skeletal sites in both pediatric and adult populations.

The oral dosage forms described herein are suitable for administration to pediatric or adult patients in need of such treatment.

In some embodiments, the compounds described herein are useful as part of hormone ablation therapy, for example, in patients suffering from breast cancer or prostate cancer. In some embodiments, the compounds described herein are useful as part of aromatase inhibitor therapy, for example in patients suffering from cancer. In some embodiments, the compounds described herein are useful as part of androgen ablation therapy, for example in patients suffering from prostate cancer or other diseases.

The oral dosage forms of the present disclosure are suitable for administration to a patient according to a continuous dosing interval of daily, weekly, three times per month, twice monthly, and monthly.

When administered for the treatment or inhibition of a particular disease state or disorder, it is understood that the effective dosage may vary depending upon the particular compound or pharmaceutically acceptable salt of the compound utilized, the mode of administration, the condition, and severity thereof, of the condition being treated, as well as the various physical factors related to the individual being treated. In therapeutic application, the compounds and pharmaceutically acceptable salts of the compounds described herein are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

The compounds and pharmaceutically acceptable salts of the compounds described herein are also useful in the manufacture of medicaments for treating a bone metabolism disorder in a mammal. Similarly, the compounds and pharmaceutically acceptable salts of the compounds described herein are also useful in the manufacture of medicaments for treating a bone metabolism disorder.

One aspect of the present disclosure, therefore, encompasses compounds, or pharmaceutically acceptable salts thereof, where the compound has a structure according to Formula I

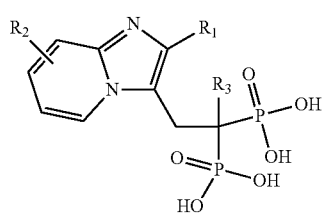

(I)

where $R_1$ is hydrogen, hydroxyl, lower alkyl, methoxy, or F; $R_2$ is hydrogen, hydroxyl, lower alkyl, or F; and $R_3$ is F, Cl, or hydrogen.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

Embodiments of this aspect of the disclosure can be, but are not limited to, compounds selected from the group consisting of: 1-fluoro-2-(imidazo[1,2-α]pyridin-3-yl-ethyl-bisphosphonic acid; 2-(imidazo[1,2-α]pyridin-3-yl)ethyl-bisphosphonic acid; 2-(6-methylimidazo[1,2-α]pyridin-3-yl)-ethyl-bisphosphonic acid; [(2-ethyl-imidazo[1,2-α]pyridin-3-yl)methyl]-bisphosphonic acid; 2-(2-t-butylimidazo[1,2-α] pyridin-3-yl)pethane-1,1- bisphosphonic acid; 2-(7-methylimidazo[1,2-α]pyridin-3-yl)-ethyl-bisphosphonic acid; [2-(8-hydroxy-imidazo[1,2-α]pyridin-3-yl)-1-ethane]-bisphosphonic acid; 2-(6-fluoroimidazo[1,2-α]pyridin-3-yl) ethyl-bisphosphonic acid; and1-fluoro-2-(7-methylimidazo [1,2-α]pyridin-3-yl)-ethyl-bisphosphonic acid, or a pharmaceutically acceptable salt thereof.

In one embodiment of this aspect of the disclosure, the compound is 1-fluoro-2-(imidazo[1,2-α]pyridin-3-yl)-ethyl-bisphosphonic acid, or a pharmaceutically acceptable salt thereof.

Another aspect of the disclosure encompasses pharmaceutical compositions that comprise a compound, or a pharmaceutically acceptable salt thereof, wherein the compound has a structure according to formula I

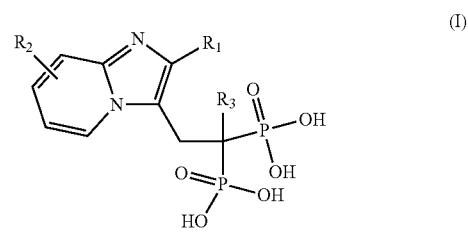

(I)

where $R_1$ is hydrogen, hydroxyl, lower alkyl, methoxy, or F; $R_2$ is hydrogen, hydroxyl, lower alkyl, or F; and $R_3$ is F, Cl, or hydrogen, and a pharmaceutically acceptable carrier.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

Embodiments of this aspect of the disclosure can be, but are not limited to, compounds selected from the group consisting of: 1-fluoro-2-(imidazo[1,2-α]pyridin-3-yl-ethyl-bisphosphonic acid; 2-(imidazo[1,2-α]pyridin-3-yl)ethyl-bisphosphonic acid; 2-(6-methylimidazo[1,2-α]pyridin-3-yl)-ethyl-bisphosphonic acid; [(2-ethyl-imidazo[1,2-α]pyridin-3-yl)methyl]-bisphosphonic acid; 2-(2-t-butylimidazo[1,2-α] pyridin-3-yl)pethane-1,1- bisphosphonic acid; 2-(7-methylimidazo[1,2-α]pyridin-3-yl)-ethyl-bisphosphonic acid; [2-(8-hydroxy-imidazo[1,2-α]pyridin-3-yl)-1-ethane]-bisphosphonic acid; 2-(6-fluoroimidazo[1,2-α]pyridin-3-yl) ethyl-bisphosphonic acid; and1-fluoro-2-(7-methylimidazo [1,2-α]pyridin-3-yl)-ethyl-bisphosphonic acid, or a pharmaceutically acceptable salt thereof.

In one embodiment of this aspect of the disclosure, the composition comprises 1-fluoro-2-(imidazo[1,2-α]pyridin-3-yl)-ethyl-bisphosphonic acid, or a pharmaceutically acceptable salt thereof, and a pharmaceutically acceptable carrier.

In other embodiments of this aspect of the disclosure, the composition can further comprise at least one pharmaceutically active ingredient other than a bisphosphonic acid, or pharmaceutically acceptable salt thereof. In these embodiments, the at least one pharmaceutically active ingredient can be selected from the group consisting of, but is not limited to, an anti-inflammatory, an immunomodulator, a chelator, a musculoskeletal anabolic agent, and a combination thereof.

Yet another aspect of the disclosure encompasses methods of modulating calcium or phosphate metabolism in a subject animal or human, the method comprising administering to the subject animal or human an effective amount of a compound, or pharmaceutically acceptable salt thereof, where the compound has a structure according to Formula I

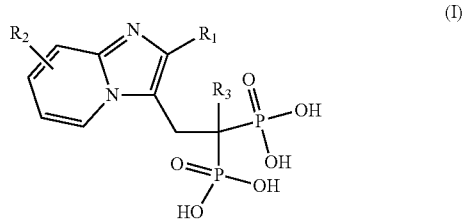

where $R_1$ is hydrogen, hydroxyl, lower alkyl, methoxy, or F; $R_2$ is hydrogen, hydroxyl, lower alkyl, or F; and $R_3$ is F, Cl, or hydrogen, whereupon the calcium or phosphate metabolism in the subject animal or human is modified.

In embodiments of the methods of this aspect of the disclosure, the calcium or phosphate metabolism in the subject animal or human before administering the compound thereto can be abnormal and associated with a skeletal disorder. In some embodiments of this aspect of the disclosure, the skeletal disorder can be selected from the group consisting of, but not limited to, osteoporosis, rheumatoid arthritis, osteoarthritis, Paget's disease, alveolar bone loss, a bone-related cancer, and an orthopedic disorder.

In other embodiments, the disorder may be a non-skeletal disorder such as, but not limited to, a non-bone cancer, an inflammatory or immunomodulatory disorder, and a parasitic disorder. In these embodiments, the parasitic disorder can be, but is not limited to, malaria, leishmaniasis, a trypanasomal disease, an entamoebal infection, a giardia infection, and a cryptosporidial infection.

In the embodiments of the methods of this aspect of the disclosure, the compound administered to the subject animal or human can modify the activity of farnesyl pyrophosphate synthase in the subject animal or human.

In the embodiments of the methods of this aspect of the disclosure, the compound, or pharmaceutically acceptable salt thereof, or is selected from the group consisting of: 1-fluoro-2-(imidazo[1,2-α]pyridin-3-yl-ethyl-bisphosphonic acid; 2-(imidazo[1,2-α]pyridin-3-yl)-ethyl-bisphosphonic acid; 2-(6-methylimidazo[1,2-α]pyridin-3-yl)ethyl-bisphosphonic acid; [(2-ethyl-imidazo[1,2-α]pyridin-3-yl)methyl]-bisphosphonic acid; 2-(2-t-butylimidazo[1,2-α]pyridin-3-yl)pethane-1,1- bisphosphonic acid; 2-(7-methylimidazo[1,2-α]pyridin-3-yl)ethyl-bisphosphonic acid; [2-(8-hydroxy-imidazo[1,2-α]pyridin-3-yl)-1-ethane]-bisphosphonic acid; 2-(6-fluoroimidazo[1,2-α]pyridin-3-yl)-ethyl-bisphosphonic acid; and 1-fluoro-2-(7-methylimidazo[1,2-α]pyridin-3-yl)-ethyl-bisphosphonic acid.

It should be noted that ratios, concentrations, amounts, and other numerical data may be expressed herein in a range format. It is to be understood that such a range format is used for convenience and brevity, and thus should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

The following examples illustrate the production of representative compounds described herein.

EXAMPLES

Example 1

3-iodo-imidazo-[1,2-α]pyridine

A solution of 11.61 g (98.27 mmol) of imidazopyridine in 100 mL of acetonitrile was placed in a 250 mL three-neck round-bottom flask equipped with a magnetic stirrer, thermocouple, nitrogen bleed, and cooling ice bath. A total of 24.32 g (108.1 mmol, 1.1 eq.) of solid N-iodosuccinimide was added portion-wise to the flask at 0° C., and the resulting yellow suspension was allowed to warm to room temperature overnight. The solvent was removed on rotavap to give the dark solid (39.2 g). This residue was re-dissolved in 0.5 L of dichloromethane and washed with 10% KOH (2×250 mL). The organic phase was separated, washed with water (200 mL), and dried over $Na_2SO_4$. The solvent was removed on rotavap, and the remaining dark material was re-crystallized from boiling ethyl acetate upon the addition of hexane. The precipitated solid was filtered, washed with 40 mL of hexane, and dried under nitrogen flow until constant weight. The yield was 20.8 g (86%) of white solid with $R_f$=0.42 (in EtOAc/hexane=1:1).

$H^1$ NMR (CDCl$_3$), δ: 8.12 (d, 1H, J=6.8 Hz), 7.69 (s, 1H), 7.62 (d, 1H, J=6.8 Hz), 7.24 (t, 1H, J=6.8 Hz), 6.94 (t, 1H, J=6.8 Hz).

$^{13}C$ NMR (CDCl$_3$), δ: 147.52, 140.02, 126.08, 125.23, 117.76, 113.43, 60.91.

LC-MS (ESI) for $C_7H_5N_2I$ m/z 245 [M+H]$^+$.

Example 2

Tetraethyl-2-(imidazo-[1,2-α]pyridin-3-yl)-ethyl-bisphosphonate

A solution of 6.67 g (27.31 mmol) of 3-iodo-imidazo-[1,2-α]pyridine (Example 1) in 200 mL of THF was placed in a 0.5 L 3-neck round bottom flask equipped with a magnetic stirrer, thermocouple, nitrogen bleed, and cooling dry ice/acetone bath. The solution was chilled on a dry ice/acetone bath, and n-BuLi (2.5M/hexane, 22 mL, 2 eq.) was gradually added at −74° C. to the white suspension (that resulted due to poor solubility of 3-iodo-imidazo-[1,2-α]pyridine at low temperature). During the addition of n-BuLi some sticky white material precipitated on the flask's walls, thus resulting in obstruction of stirring. After twenty minutes a total of 8.15 g (27.14 mmol) of the vinyl phosphonate, tetraethyl ethene-1,1-bisphosphonate (prepared according to literature procedures J. Org. Chem., 51: 3488-3490 (1986)), in 20 mL of THF was introduced into a flask at −75° C. A sticky semisolid gradually dissolved, and the color of the reaction mixture turned almost black. After 30 minutes of stirring at −75° C., the reaction was allowed to gradually warm to −40° C. and then was quenched by slow addition of 200 mL of saturated NH$_4$Cl. The resulting mixture was warmed to ambient temperature, the organic layer was separated, and the aqueous phase extracted with ethyl acetate (3×100 mL). The combined organic phases were washed with brine (100 mL), dried over Na$_2$SO$_4$, and concentrated on rotavap to give 8.1 g of dark oil. This oil was purified by CombiFlash on silica gel and after concentration of pure fractions (purity was checked by $^{31}$P NMR) a total of 1.7 g (15% yield) of pure tetraethyl-2-(imidazo-[1,2-α]pyridin-3-yl)ethyl-bisphosphonate was isolated as a dark oil with $R_f$=0.18 in EtOAc/MeOH=8:2.

$^1$H NMR (CDCl$_3$), δ: 8.23 (d,1H, J=7.2 Hz), 7.60 (d, 1H, J=9.2 Hz), 7.53 (s,1H), 7.16 (dd, 1H, J=9.2, J=7.2 Hz), 6.84 (t, 1H, J=6.8 Hz), 4.11 (m, 8H), 3.57 (td, 2H, $^3J_{HH}$=6.2, $^3J_{PH}$=15.6 Hz), 2.63 (tt, 1H, $^3J_{HH}$=6.2, $^2J_{PH}$=23.6 Hz), 1.27 (q, 12H, $^3J_{HH}$=7.2 Hz).

$^{13}$C NMR (CDCl$_3$), δ: 145.3, 133.0, 123.55, 123.52, 121.3 (t, $^3J_{CP}$=8.0 Hz), 117.9, 112.1, 62.9 (d, $^2J_{COP}$=6.6 Hz), 62.7 (d, $^2J_{COP}$=6.6 Hz), 36.1 (t, $J_{CP}$=132.8 Hz), 20.0 (t, $^2J_{CP}$=4.8 Hz), 16.3, 16.2.

$^{31}$P NMR (CDCl$_3$), δ: 22.2. LC-MS (ESI) for C$_{17}$H$_{28}$N$_2$O$_6$P$_2$ m/z 419 [M+H]$^+$.

Example 3

Tetraethyl-1-fluoro-2-(imidazo-[1,2-α]pyridin-3-yl)-ethyl-bisphosphonate

A 30% suspension of KH in paraffin oil (0.9965 g, 7.45 mmol, 1.83 eq.) was charged in a 50 mL three-neck round bottom flask equipped with a magnetic stirrer, thermocouple, nitrogen line, and cooling bath. Anhydrous THF (15 mL) was added into the flask, and the resulting suspension was chilled to 0° C. A solution of the bisphosphonate tetraethyl-2-(imidazo-[1,2-α]pyridin-3-yl)-ethyl-bisphosphonate (Example 2) (1.6955 g, 4.05 mmol) in 15 mL of THF was slowly added to the suspension of KH, and the resulting brown-colored solution was brought to ambient temperature in 30 minutes. A catalytic amount of 18-crown-6 (0.3275 g, 1.23 mmol, 30 mol%) was added to the reaction, and after 5 minutes of stirring the mixture was chilled to 0° C. A total of 3.0785 g (8.68 mmol, 2.1 eq.) of SELECTFLUOR® was added portion wise at 0° C., and the mixture stirred at this temperature until all starting material was consumed (about 3-5 hours). The reaction was monitored by TLC (EtOAc/MeOH=8:2), and after completion it was quenched with ice-cold saturated NaHCO$_3$ solution (50 mL). The product was extracted with ethyl acetate (3×50 mL), and the combined organic phases were washed with brine (30 mL) and dried over Na$_2$SO$_4$. After concentration under reduced pressure a total of 1.92 g of dark oil was obtained. This crude material was purified on silica gel using ethyl acetate and ethyl acetate/MeOH=9:1 mixtures as eluent to give 1.164 g of clear amber oil. According to $^{31}$P NMR, this oil was contaminated with an elimination product possessing essentially the same R$_f$ value as the desirable product tetraethyl-1-fluoro-2-(imidazo-[1,2-α]pyridin-3-yl)-ethyl-bisphosphonate. Therefore, it was further purified by preparative HPLC (a total of 6 runs were completed). After concentration of "good" fractions and freeze-drying a total of 0.6791 g (38% yield) of pure tetraethyl-1-fluoro-2-(imidazo-[1,2-α]pyridin-3-yl)-ethyl-bisphosphonate was isolated.

Example 4

3-yl)-ethyl-bisphosphonic acid (23)

A solution of tetraethyl-1-fluoro-2-(imidazo-[1,2-α]pyridin-3-yl)-ethyl-bisphosphonate (0.6465 g, 1.48 mmol) in 10 mL of anhydrous chloroform was placed in a 50 mL 3-neck round bottom flask equipped with a magnetic stirrer, thermocouple, condenser, heating mantle, and nitrogen bleed. Neat TMSBr (2.0973 g, 13.69 mmol, approximately 9 eq.) was added to this solution at room temperature, and the resulting solution stirred at 50° C. until only the mass M−1=323 was observed in LC-MS in negative mode (usually complete deprotection requires 20-24 hours). The reaction mixture was cooled to room temperature and concentrated on rotavap to give 0.6887 g of yellow oil. This oil was dissolved in 5 mL of anhydrous chloroform and filtered through the 0.45μ PTFE membrane filter to give a clear yellow solution. A total of 5 mL of DI water was slowly added to this solution followed by slow addition of acetonitrile (about 15 mL) until crystallization occurred. The resulting suspension was stirred for 30 minutes at room temperature and then filtered through a fine sintered glass filter. The isolated solid was washed with water (2×3 mL) following by methanol (2×3 mL) and anhydrous ether (2×5 mL) washes. After drying under suction and nitrogen blanket the white solid was additionally dried overnight in a drying apparatus over phosphorous pentoxide under vacuum (1.5 mm Hg) at 40° C. The yield was 240 mg (50%) of 23 as a white solid, having the following structure:

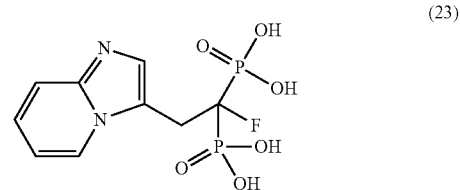 [SMILES: O=P(O)(O)C(F)(Cc1cnc2ccccn12)P(=O)(O)O]

(23)

Elemental analysis (%) calculated for C$_9$H$_{11}$FN$_2$O$_6$P$_2$·0.5H$_2$O (333.15): C 32.45, H 3.63, N 8.41. Found C 32.39, H 3.54, N 8.23.

$^1$H NMR (300 MHz, D$_2$O+KOD, ppm): 3.76 (tt, 2H, J=21.6, 11.7), 6.92 (t, 1H, J=6.6 Hz), 7.28 (m, 1H), 7.59-7.47 (m, 2H).

$^{13}$C NMR (75 MHz, D$_2$O+KOD, ppm): 28.64 (d, J=18.8), 87.63, 99.43, 100.0, 101.23, 101,81, 103.60, 111.88, 115.22, 123.15, 123.23, 124.98, 126.25, 126.31, 132.07, 144.92.

$^{31}$P NMR (121 MHz, D$_2$O+KOD, ppm): 13.57 (d, J=66 Hz).

$^{19}$F NMR (282 MHz, D$_2$O+KOD, ppm): −182.36 (m, J=67 Hz, 21 Hz).

MS(ESI) 323 (M−1)

Example 5

2-(imidazo-[1,2-α]pyridin-3-yl)-ethyl-bisphosphonic acid (80)

Trimethyl silylbromide (TMSBr, 9.7 mL, 75.1 mmol) was added to a solution of tetraethyl-2-(imidazo-[1,2-α]pyridin-3-yl)-ethyl-bisphosphonate (Example 2) (3.15 g, 7.5 mmol) in anhydrous chloroform (35 mL) and reaction mixture was stirred at 40° C. under inert atmosphere overnight. Solvent and excess of TMSBr were removed and the resulting tawny residue was dissolved in water (50 mL). The aqueous solution was stirred at room temperature for 5 hours and refrigerated over night. White precipitate was filtered, washed consequently with methanol/water (1:1), acetonitrile, dichloromethane, and dried in high vacuum. Yield 1.85 g (80%) of target 1 as white powder.

$^1$H NMR (D$_2$O), δ: 8.53 (d,1H, J=6.8 Hz), 7.56 (d, 1H, J=9.2 Hz), 7.53 (s,1H), 7.36 (dd, 1H, J=9.2, J=6.8 Hz), 7.03 (t, 1H, J=6.8 Hz), 3.35 (td, 2H, $^3J_{HH}$=5.6, $^3J_{PH}$=14.5 Hz), 2.23 (tt, 1H, $^3J_{HH}$=5.6, $^2J_{PH}$=21.6 Hz).

$^{13}$C NMR (D$_2$O), δ: 144.93, 129.51, 127.37 (t, $^3J_{CP}$=8.0 Hz), 125.06, 125.02, 115.57, 112.30, 38.97 (t, $J_{CP}$=128.0 Hz), 22.77.

$^{31}$P NMR (D$_2$O), δ: 19.87. LC-MS (ESI) for C$_9$H$_{12}$N$_2$O$_6$P$_2$ m/z 305 [M-H]. Calc. for C$_9$H$_{12}$N$_2$O$_6$P$_2$.0.1 CF$_3$CO$_2$H (%): C 34.80, H 3.84, N 8.82; found (%): C 34.74, H 3.84, N 8.95.

Example 6

3-Iodo-6-methylimidazo[1,2-α]pyridine

3-Iodo-6-methyl imidazo[1,2-α]pyridine was prepared according to the procedure of Examples 1 and 5 using 6-methylimidazo[1,2-α]pyridine as a starting material. Yield 82%, white solid.

H$^1$ NMR (CDCl$_3$), δ: 7.88 (s, 1H), 7.62 (s, 1H), 7.51 (d, 1H, J=9.3 Hz), 7.08 (d, 1H, J=8.7 Hz), 2.38 (s, 3H).

Example 7

Tetraethyl-2-(6-methylimidazo[1,2-α]pyridin-3-yl)-ethyl-bisphosphonate

Tetraethyl-2-(6-Methylimidazo-[1,2-α]pyridin-3-yl)-ethyl-bisphosphonate was prepared according to the procedure of Example 2. Yield 36%, yellow oil.

$^1$H NMR (CDCl$_3$), δ: 7.97 (s, 1H), 7.53 (d,1H, J=9.0 Hz), 7.45 (s,1H), 7.30 (d, 1H, J=9.0 Hz), 4.10 (m, 8H), 3.51 (td, 2H, $^3J_{HH}$=6.0, $^3J_{PH}$=15.6 Hz), 2.60 (tt, 1H, $^3J_{HH}$=6.0, $^2J_{PH}$=23.5 Hz), 2.33 (s, 3H), 1.24 (m, 12H).

$^{31}$P NMR (CDCl$_3$), δ: 23.06. FI-MS (ESI) for C$_{18}$H$_{30}$N$_2$O$_6$P$_2$ m/z 433 [M+H]$^+$.

Example 8

2-(6-methylimidazo-[1,2-α]pyridin-3-yl)-ethyl-bis-phosphonic acid (81)

2-(6-Methylimidazo-[1,2-α]pyridin-3-yl)ethyl-bisphosphonic acid was prepared according to the procedure of Example 5. The product precipitated from aqueous solution and a white precipitate was filtered, washed consequently with water, methanol, ether, and dried in high vacuum. Yield 74% of 2-(6-methylimidazo-[1,2-α]pyridin-3-yl)ethyl-bisphosphonic acid as white crystals.

$^1$H NMR (D$_2$O), δ: 8.22 (s, 1H), 7.38 (s, 1H), 7.37 (d, 1H, J=9.3 Hz), 7.13 (d, 1H, J=9.3 Hz), 3.20 (td, 2H, $^3J_{HH}$=5.5, $^3J_{PH}$=13.8 Hz), 2.28 (s, 3H), 2.14 (tt, 1H, $^3J_{HH}$=5.5, $^2J_{PH}$=21.9 Hz).

$^{31}$P NMR (D$_2$O), δ: 20.08. LC-MS (ESI) for C$_{10}$H$_{14}$N$_2$O$_6$P$_2$ m/z 319 [M-H]$^-$. Calc. for C$_{10}$H$_{14}$N$_2$O$_6$P$_2$ (%): C 37.51, H 4.41, N 8.75; found (%): C 37.27, H 4.21, N 8.57.

Example 9

Tetraethyl-2-(7-methyl)-imidazo-[1,2-α]pyridin-3-yl-ethyl-bisphosphonate (9)

Tetraethyl-2-(7-methyl)-imidazo-[1,2-α]pyridin-3-yl-ethyl-bisphosphonate was prepared according to a process as described in Examples 1 and 2. $^1$H NMR (CDCl$_3$), δ: 8.11 (d,1H, J=7.0 Hz), 7.42 (s,1H), 7.41 (d, 1H, J=8.7 Hz), 6.69 (d, 1H, J=7.0 Hz), 4.10 (m, 8H), 3.51 (td, 2H, $^3J_{HH}$=6.3, $^3J_{PH}$=15.8 Hz), 2.57 (tt, 1H, $^3J_{HH}$=6.3, $^2J_{PH}$=23.4 Hz), 2.38 (s, 3H), 1.25 (m, 12H).

$^{31}$P NMR (CDCl$_3$), δ: 23.3. FI-MS (ESI) for C$_{18}$H$_{30}$N$_2$O$_6$P$_2$ m/z 433 [M+H]$^+$.

Example 10

Tetraethyl-1-fluoro-2-(7-methyl)-imidazo-[1,2-α] pyridin-3-yl-ethyl-bisphosphonate (10)

As schematically shown in FIG. 3, a 30% suspension of KH in paraffin oil (0.2957 g, 2.21 mmol, 1.85 eq.) was charged in a 50 mL three-neck round bottom flask equipped with a magnetic stirrer, thermocouple, nitrogen line, and cooling bath. Anhydrous THF (16 mL) was added into the flask, and the resulting suspension was chilled to 0° C. A solution of tetraethyl-2-(7-methyl)-imidazo-[1,2-α]pyridin-3-yl-ethyl-bisphosphonate (9) (Example 9) (0.5155 g, 1.192 mmol) in 6 mL of THF was slowly added to the suspension of KH, and the resulting brown solution was brought to ambient temperature in 30 min. A catalytic amount of 18-crown-6 (0.082 g, 0.31 mmol, 26 mol %) was added to the reaction, and after 5 min of stirring the mixture was chilled to 0° C. A total of 0.8453 g (2.386 mmol, 2.0 eq.) of SELECTFLUOR® was added portion-wise at 0° C., and the mixture stirred at this temperature until all starting material was consumed (overnight). The reaction was monitored by TLC and after completion it was quenched with ice-cold saturated NaHCO$_3$ solution (50 mL). The pH of the mixture was adjusted to 9 with solid Na$_2$CO$_3$, and the product was extracted with ethyl acetate (3×20 mL).

The combined organic phases were washed with brine (20 mL), dried over Na$_2$SO$_4$, and after concentration under reduced pressure a total of 0.8586 g of dark oil was obtained. This crude material was purified on silica gel using ethyl acetate and ethyl acetate/MeOH=9:1 mixtures as eluent to give 0.2725 g (50.8% yield) of a clear yellow oil.

Example 11

1-fluoro-2-(7-methyl)-imidazo-[1,2-α]pyridin-3-yl-ethyl-bisphosphonic acid (11)

As schematically shown in FIG. 3, a solution of tetraethyl-1-fluoro-2-(7-methyl)-imidazo-[1,2-α]pyridin-3-yl-ethyl-bisphosphonate (10) (Example 10) (0.2725 g, 0.605 mmol) in 5 mL of anhydrous chloroform was placed in a 25 mL 3-neck round bottom flask equipped with a magnetic stirrer, thermocouple, condenser, heating mantle, and nitrogen bleed. Neat TMSBr (0.6191 g, 3.922 mmol, approximately 6.5 eq.) was added to this solution at room temperature, and the resulting solution stirred at 50° C. until only the mass M−1=337 was observed in LC-MS in negative mode (required about 2 days). The reaction mixture was cooled to room temperature and concentrated by rotavap. A total of 4 mL of water was added to the residue, and the obtained cloudy solution was quickly filtered using a 0.45 micron membrane filter attached to the syringe. The aqueous solution was diluted with acetonitrile (approximately 20 mL) and stirred at 0° C. overnight. The slowly formed precipitate was filtered, washed with water (2×5 mL), methanol (2×5 mL), and finally with ether. The residue dried under suction and then under high vacuum at 40° C. overnight to give 76 mg (38% yield) of 1-fluoro-2-(7-methyl)-imidazo-[1,2-α]pyridin-3-yl-ethyl-bisphosphonic acid as a white solid.

Elemental analysis (%) calcd for C$_{10}$H$_{13}$FN$_2$O$_6$P$_2$.0.5H$_2$O (347.18): C 34.60, H 4.06, N 8.07; Found: C 34.63, H 4.09, N 8.05.

¹H NMR (300 MHz, D₂O+KOD, ppm): 2.32 (s, 3H), 3.68 (m, 2H, J=21.6 Hz, 10.8 Hz), 6.75 (d, 1H, J=6.3 Hz), 7.22 (s, 1H), 7.38 (s, 1H), 8.47 (d, 1H, J=7.2 Hz).
13C NMR (75 MHz, D₂O₊KOD, ppm): 20.21, 20.47, 28.73, 113.45, 113.71, 114.45, 114.71, 122.84, 125.48, 125.74, 131.50, 131.74, 136.55, 136.81, 145.68.
31P NMR (121 MHz, D₂O₊KOD, ppm): 13.82 (d, J=66 Hz).
¹⁹F NMR (282 MHz, D₂O+KOD, ppm): −182.39 (m J=64.5 Hz, 24 Hz)
MS(ESI) 337 (M−1)

Example 12

3-Iodo-7-methyl imidazo[1,2-α]pyridine (13)

Figure 4:
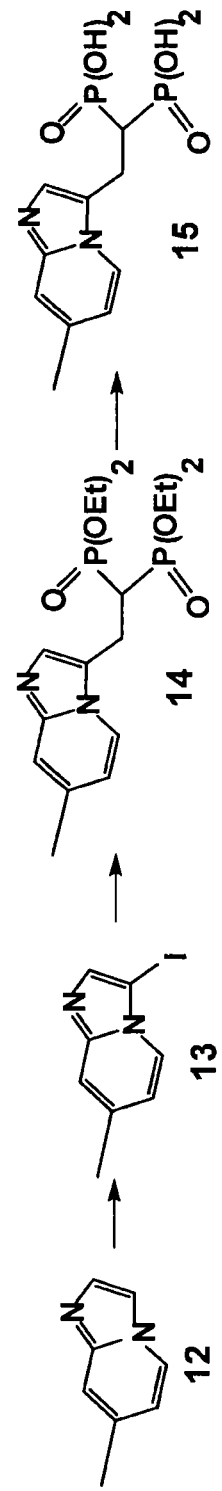
FIG. 4 schematically illustrates a process for making 2-(7-methyl)-imidazo-[1,2-α]pyridin-3-yl-ethyl-bisphosphonic acid.

As shown in FIG. 4, 3-Iodo-7-methyl imidazo[1,2-α]pyridine (13) was prepared according to the procedure of Examples 1 and 5 using 7-methylimidazo[1,2-α]pyridine (12) as a starting material.
H¹ NMR (CDCl₃), δ6: 7.96 (d, 1H, J=7.2 Hz), 7.61 (s, 1H), 7.35 (s, 1H), 6.72 (d, 1H, J=7.2 Hz), 2.41 (s, 3H).
13C NMR (CDCl₃), δ6: 147.90, 139.81, 135.82, 124.97, 116.10, 115.72, 59.47, 21.08.

Example 13

Tetraethyl-2-(7-methyl)-imidazo-[1,2-α]pyridin-3-yl-ethyl-bisphosphonate (14)

As shown in FIG. 4, tetraethyl-2-(7-methyl)-imidazo-[1,2-α]pyridin-3-yl-ethyl-bisphosphonate (14) was prepared similarly to Example 2 but 40% of starting 3-iodo-7-methyl imidazo[1,2-α]pyridine (Example 12) was recovered after chromatographic purification of the product. Yield 46%, yellow oil.
¹H NMR (CDCl₃), δ: 8.11 (d,1H, J=7.0 Hz), 7.42 (s,1H), 7.41 (d, 1H, J=8.7 Hz), 6.69 (d, 1H, J=7.0 Hz), 4.10 (m, 8H), 3.51 (td, 2H, ³J$_{HH}$=8.3, ³J$_{PH}$=15.8 Hz), 2.57 (tt, 1H, ³J$_{HH}$=8.3, ²J$_{PH}$=23.4 Hz), 2.38 (s, 3H), 1.25 (m, 12H).
31P NMR (CDCl₃), δ: 23.3.
FI-MS (ESI) for C₁₈H₃₀N₂O₆P₂ m/z 433 [M+H]⁺.

Example 14

2-(7-methyl)-imidazo-[1,2-α]pyridin-3-yl-ethyl-bisphosphonic acid (15)

As shown in FIG. 4, 2-(7-methyl)-imidazo-[1,2-α]pyridin-3-yl-ethyl-bisphosphonic acid (15) was prepared according to the procedure of Example 4 using tetraethyl-2-(7-methyl)-imidazo-[1,2-α]pyridin-3-yl-ethyl-bisphosphonate as a starting material. Yield 87%, white powder.
¹H NMR (D₂O), δ: 8.39 (d, 1H, J=6.9 Hz), 7.40 (s, 1H), 7.31 (s, 1H), 6.87 (d, 1H, J=7.2 Hz), 3.29 (td, 2H, ³J$_{HH}$=5.4, ³J$_{PH}$=15.2 Hz), 2.40 (s, 3H), 2.19 (tt, 1H, ³J$_{HH}$=5.4, ²J$_{PH}$=21.6 Hz).
³¹ NMR (D₂O), δ: 20.04.
FI-MS (ESI) for C₁₀H₁₄N₂O₆P₂ m/z 319 [M-H]⁻.
Calc. for C₁₀H₁₄N₂O₆P₂ 0.5 CF₃CO₂H 0.8 H₂O (%): C 33.74, H 4.14, N 7.15
Found (%): C 33.67, H 4.14, N 7.04.

Example 15

6-fluoro-imidazo[1,2-α]pyridine (26)

Figure 5:
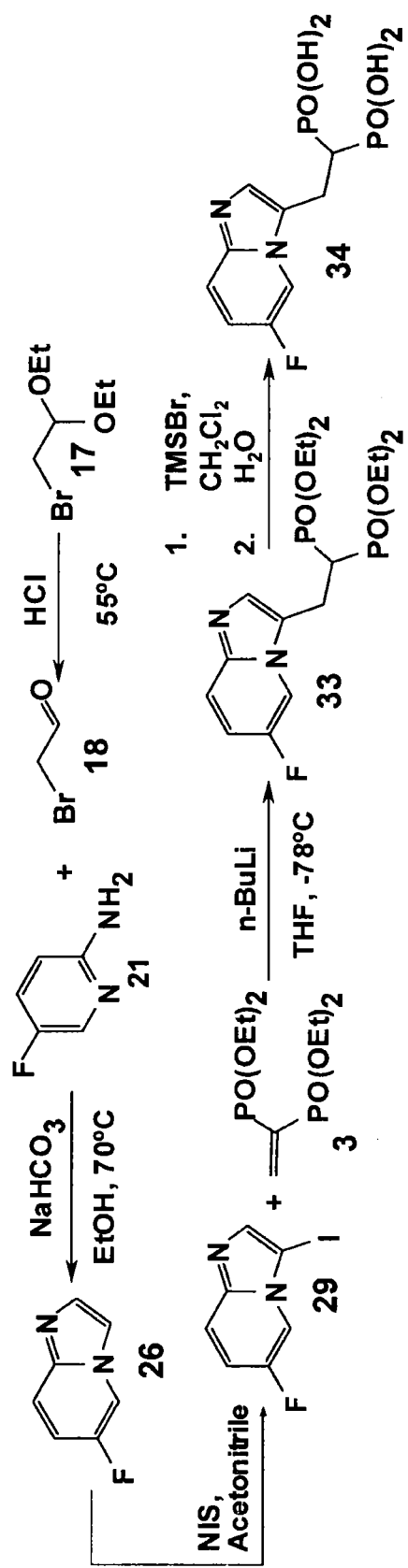
FIG. 5 schematically illustrates a process for making [2-(6-fluoro-imidazo[1,2-a]pyridin-3-yl)-ethyl]-bisphosphonic acid (34).

Synthesis of 6-fluoro-imidazo[1,2-a]pyridine (26) is shown schematically in FIG. 5. Concentrated HCl (34 mL, 345 mmol) was added drop-wise to 2-bromo-1,1-diethoxy-ethane 17 (26.37 g, 133.8 mmol) at room temperature in a 250-mL three neck round bottomed flask. The mixture was then heated at 55° C. for 30 minutes. The pale yellow mixture was then cooled to 0° C. and excess anhydrous Na₂SO₄ (64 g) added and the reaction stirred for 1.0 hr. The reaction mixture now containing crude bromoacetaldehyde 18 was filtered into a three neck 1000 mL round bottomed flask and the cake washed with ethanol (100 mL). The flask was then cooled to 0° C. and 2-amino-5-fluoropyridine (10.0 g, 50 mmol) added portion-wise followed by the addition of NaHCO₃ (42 g, 500 mmol). There was evolution of gas. After the bubbling had ceased, the mixture was refluxed at 70° C. for 1.0 hour. The reaction mixture was then cooled to room temperature, filtered and concentrated under reduced pressure. CH₂Cl₂ was added to the residue at 0° C. and 40% NaOH (30 mL) added to pH 10. The mixture was then diluted with water (100 mL) and the organic phase separated, dried (Na₂SO₄) and concentrated under reduced pressure. Purification on silica gel (CombiFlash, Heptanes/EtOAc elution) afforded 6-fluoro-imidazo[1,2-α]pyridine 26 as a brown solid. 5.52 g, 85%, yield.
¹H NMR (300 MHz, CDCl₃, 297K) δ 7.06 (m, 1H), 7.56 (m, 3H), 8.04 (m, 1H).
¹⁹F NMR (282.2 MHz, CDCl₃, 297K) 6:21.61.
ESI MS (MeOH) calcd for C₇H₅FN₂ 136.13, found m/z (M⁺+1) 137.

Example 16

6-fluoro-3-iodo-imidazo[1,2-α]pyridine (29)

As shown in FIG. 5, 6-Fluoro-3-iodo-imidazo[1,2-α]pyridine (29) was prepared according to a literature procedure (Enguehard et al., *J. Org. Chem.* 65: 6572-6575 (2000), incorporated herein by reference in its entirety). N-iodosuccinimide (9.2 g, 40.8 mmol) was added to a solution of 6-fluoro-imidazo[1,2-α]pyridine 26 (Example 15) (7.6 g, 40.8 mmol) in dry acetonitrile (100 mL) at 0° C. The reaction was warmed to room temperature and then stirred for 12 hours. The mixture was filtered and the cake washed with acetonitrile and water and dried under high vacuum to afford 6-fluoro-3-iodo-imidazo[1,2-α]pyridine 29 off white solid. 8.5 g, 88% yield.
¹H NMR (300 MHz, CDCl₃, 297K) δ 7.14 (td, J=2.1, 7.8 Hz, 1H), 7.59 (dd, J=5.1, 9.9 Hz, 1H), 7.72 (s, 1H), 8.07 (distorted t, J=3.0 Hz, 1H).
ESI MS (MeOH) calcd for C₇H₄FIN₂ 262.03, found m/z (M⁺+1) 263.

Example 17

[1-(diethoxy-phosphoryl)-2-(6-fluoro-imidazo[1,2-α]pyridin-3-yl)-ethyl]-phosphonic acid diethyl ester (33)

As shown in FIG. 5, [1-(Diethoxy-phosphoryl)-2-(6-fluoro-imidazo[1,2-α]pyridin-3-yl)-ethyl]-phosphonic acid diethyl ester was prepared in accordance with an adapted literature procedure (Inoue et al., Synthesis 13:1971-1976 (2003)). 6-Fluoro-3-iodo-imidazo[1,2-α]pyridine 29 (Example 16) (8.0 g, 30.5 mmol) in anhydrous THF (200 mL) was stirred at −78° C., under argon, then n-BuLi (2.5 M, 24.4 mL, 61 mmol) in hexanes was added slowly, keeping the temperature below -70° C. The resulting mixture was stirred for 10 minutes, then tetraethyl ethane-1,1-bisphosphonate 3 (9.16 g, 30.5 mmol) in anhydrous THF (25 mL) was added slowly, keeping the temperature below −70° C. The reaction mixture was stirred for an additional 10 minutes, cooled to room temperature, then quenched with saturated NH$_4$Cl (100 mL). The mixture was then extracted with CH$_2$Cl$_2$ (200 mL×3) and the organic phase washed with water (200 mL×2). The resultant organic phase was then dried with Na$_2$SO$_4$, concentrated under reduced pressure and purified on silica gel (CombiFlash, EtOAc/MeOH elution) to afford [1-(diethoxy-phosphoryl)-2-(6-fluoro-imidazo[1,2-α]pyridin-3-yl)-ethyl]-phosphonic acid diethyl ester 33 as yellow oil. 1.0 g, 8% yield.

$^1$H NMR (300 MHz, CDCl3, 297K) δ 1.03 (m, 12H), 2.36 (tt, J=6.0, 17.7 Hz, 1H, PCHP), 3.33 (dt, J=9.9, 15.6 Hz, 2H, CH2), 4.00 (m, 8H), 6.84 (t, J=7.5 Hz, 1H), 7.30 (m, 2H), 7.99 (s, 1H).

$^{13}$C NMR (75.5 MHz, CDCl3, 297K) δ: 16.14 (d, J=6.04 Hz), 20.02 (t, J=4.9 Hz), 35.86 (t, J=132.12 Hz), 62.82 (dd, J=6.72, 17.06 Hz), 110, 110.52, 118.1 (d, J=9.13 Hz), 122.74, 134.37, 142.91, 151.63, 154.77.

$^{19}$F NMR (282.2 MHz, CDCl3, 297K) δ:−140.77.

31P (121.5 MHz, CDCl3, 297K) δ 22.79.

ESI MS (MeOH) calcd for C17H27FN2O6P2 436.36, found m/z (M++1) 437.

Example 18

[2-(6-fluoro-imidazo[1,2-α]pyridin-3-yl)-ethyl]-bisphosphonic acid (34)

The full synthesis of (34) is illustrated schematically in FIG. 5. To a stirred solution of [1-(diethoxy-phosphoryl)-2-(6-fluoro-imidazo[1,2-α]pyridin-3-yl)-ethyl]-phosphonic acid diethyl ester 33 (Example 17) (1.0 g, 2.2 mmol) in dry CH$_2$Cl$_2$ (10 mL) under argon was added bromotrimethylsilane (3.4 mL, 26.4 mol) and the mixture stirred at room temperature for 24 hours. The reaction mixture was concentrated in vacuo and the residue dissolved in CH$_2$Cl$_2$ (10 mL) then H$_2$O (8.0 mL) was added. The aqueous layer was separated and purified on HPLC to afford [2-(6-fluoro-imidazo[1,2-α]pyridin-3-yl)-ethyl]-bisphosphonic acid 34 as colorless solid. 500 mg, 70% yield.

$^1$H NMR (300 MHz, D$_2$O+1 drop KOD, 297K) δ 2.19 (tt, J=7.1, 22.8 Hz, 1H, CH), 3.45 (dt, J=7.4, 17.2 Hz, 2H, CH$_2$), 7.21 (m,1H), 7.5 (m, 2H), 8.5 (s, 1H)

$^{31}$P (121.5 MHz, D$_2$O+1 drop KOD, 297K) δ 19.68.

ESI MS (D$_2$O) calcd for C$_9$H$_{11}$N$_2$O$_6$FP$_2$ 324.14, found m/z (M$^+$−1) 323.

Example 19

8-benzyloxy-imidazo[1,2-α]pyridine (24)

Figure 6:
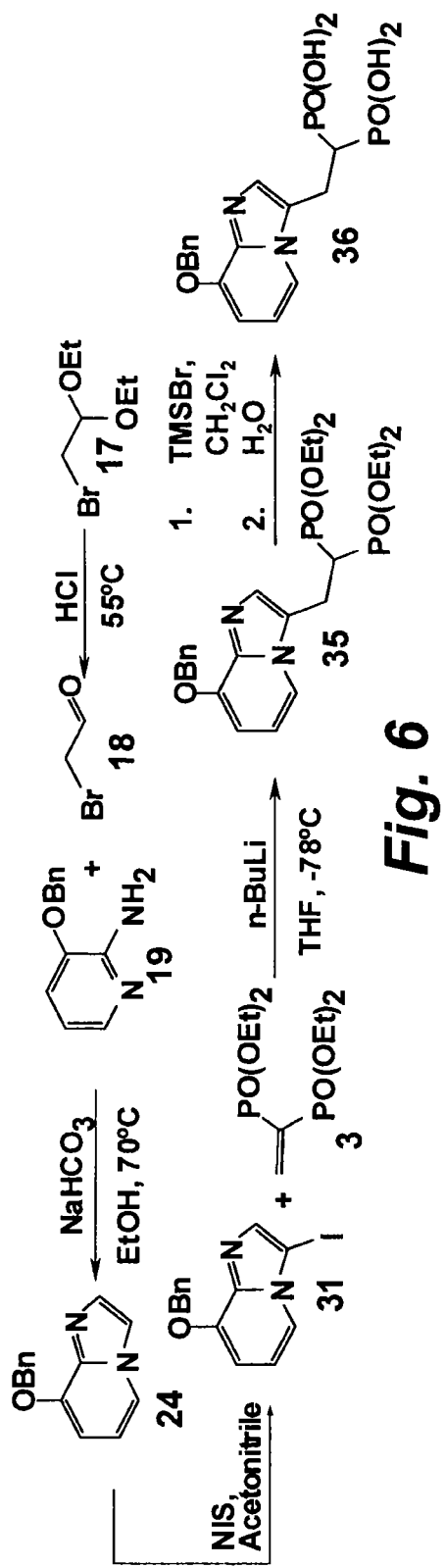
FIG. 6 schematically illustrates a process for making 2-(8-(benzyloxy)imidazo[1,2-α]pyridin-3-yl)-1-ethane-bisphosphonic acid (36).

As shown in FIG. 6, concentrated HCl (34 mL, 345 mmol) was added drop-wise to 2-bromo-1,1-diethoxyethane 17 (29.56, 150 mmol) at room temperature in a 250-mL three neck round bottomed flask. The mixture was then heated at 55° C. for 30 minutes. The pale yellow mixture was then cooled to 0° C. and anhydrous Na$_2$SO$_4$ (64 g) added and the reaction stirred for 1.0 hour. The reaction mixture now containing crude bromoacetaldehyde 18 was filtered into a three neck 1000-mL round bottomed flask and the cake washed with ethanol (100 mL). The flask was then cooled to 0° C. and 2- amino-3-benzyloxypyridine 19 (10.0 g, 50 mmol) added portion wise followed by the addition of NaHCO$_3$ (42 g, 500 mmol). There was evolution of gas. After the bubbling had ceased, the mixture was refluxed at 70° C. for 1.0 hour. The reaction mixture was then cooled to room temperature, filtered and concentrated under reduced pressure. CH$_2$Cl$_2$ was added to the residue at 0° C. and 40% NaOH (30 mL) added to pH 10. The mixture was then diluted with water (100 mL) and the organic phase separated, dried (Na$_2$SO$_4$) and concentrated under reduced pressure. Purification on silica gel (CombiFlash, Heptanes/EtOAc elution) afforded 8-benzyloxy-imidazo[1,2-α]pyridine 24 as colorless needles. 7.2 g, 64%, yield.

$^1$H NMR (300 MHz, CDCl$_3$, 297K) δ 5.09 (s, 2H), 6.22 (d, J=7.8 Hz, 1H), 6.37 (t, J=6.9 Hz, 1H), 7.14 (m, 3H), 7.29 (m, 3H), 7.37 (s, 1H), 7.51 (d, J=6.6 Hz, 1H).

$^{13}$C NMR (75.5 MHz, CDCl$_3$, 297K) δ:70.62, 102.45, 112.12, 113.34, 118.89, 127.42, 128.05, 128.60, 132.73, 136.26, 148.20.

ESI MS (MeOH) calcd for C$_{14}$H$_{12}$N$_2$O 224.26, found m/z (M$^+$+1) 225.

Example 20

8-benzyloxy-3-iodo-imidazo[1,2-α]pyridine (31)

As shown in FIG. 6, N-iodosuccinimide (7.0 g, 31.2 mmol) was added to a solution of 8-benzyloxy-imidazo[1,2-α]pyridine (Example 19) 24 (7.0 g, 31.2 mmol) in dry acetonitrile (100 mL) at 0° C. The reaction was warmed to room temperature and then stirred for 12 hours. The mixture was filtered and the cake washed with acetonitrile and water and dried under high vacuum to afford 8-benzyloxy-3-iodo-imidazo[1, 2-α]pyridine 31 as colorless solid. 9.0 g, 83%, yield.

$^1$H NMR (300 MHz, CDCl$_3$, 297K) δ5.11 (s, 2H), 6.33 (d, J=7.5 Hz, 1H), 6.55 (t, J=7.35 Hz, 1H), 7.13 (m, 3H), 7.28 (d, J=6.9 Hz, 2H), 7.45 (s, 1H), 7.54 (d, J=6.6 Hz, 1H).

$^{13}$C NMR (75.5 MHz, CDCl$_3$, 297K) δ:70.89, 103.23, 112.95, 119.15, 127.44, 128.18, 128.67, 135.98, 139.41, 142.16, 147.84.

ESI MS (MeOH) calcd for C$_{14}$H$_{11}$IN$_2$O 350.16, found m/z (M$^+$+1) 351.

Example 21

[2-(8-benzyloxy-imidazo[1,2-α]pyridin-3-yl)-1-(diethoxy-phosphoryl)-ethyl]-phosphonic acid diethyl ester (35)

As shown in FIG. 6, 8-Benzyloxy-3-iodo-imidazo[1,2-α]pyridine 31 (Example 20).(7.0 g, 20 mmol) in anhydrous THF (200 mL) was stirred at −78° C., under argon, then n-BuLi (2.5 M, 16.0 mL, 40 mmol) in hexanes was added slowly, keeping the temperature below −70° C. . The resulting mixture was stirred for 10 min, then tetraethyl ethene-1,1-bisphosphonate 3 (6.0 g, 20.0 mmol) in anhydrous THF (20 mL) was added slowly, keeping the temperature below −70° C. The reaction mixture was stirred for an additional 10 minutes, cooled to room temperature, and then quenched with saturated NH$_4$Cl (100 mL). The mixture was then extracted with CH$_2$Cl$_2$ (200 mL×3) and the organic phase washed with water (200 mL×2). The resultant organic phase was then dried with Na$_2$SO$_4$, concentrated under reduced pressure and purified on silica gel (CombiFlash, EtOAc/MeOH elution) to afford [2-(8-Benzyloxy-imidazo[1,2-α]pyridin-3-yl)-1-(diethoxy-phosphoryl)-ethyl]-phosphonic acid diethyl ester 35 as yellowish brown oil. 7.18 g, 69% yield.

$^1$H NMR (300 MHz, CDCl$_3$, 297K) δ: 1.04 (m, 12H, OCH$_2$CH$_3$), 2.41 (tt, J=6.0, 17.4 Hz, 1H, PCHP), 2.30 (dt, J=9.6, 15.6 Hz, 2H, PCHCH$_2$), 3.89 (m, 8H, OCH$_2$CH$_3$), 5.08 (s, 2H, PhCH$_2$Ar) 6.24 (d, J=7.5 Hz, 1H), 6.45 (t, J=7.05 Hz, 1H), 7.13 (m, 3H), 7.25 (m, 3H), 7.62 (d, J=6.9 Hz, 1H).

$^{13}$C NMR (75.5 MHz, CDCl$_3$, 297K) δ: 16.30 (d, J=6.12 Hz), 20.28 (t, J=4.79 Hz), 36.05 (t, J=132.50 Hz, PCP), 62.85 (dd, J=6.78, 17.14 Hz), 70.57, 102.10, 112.08, 116.67, 122.32 (t, J=8.00 Hz), 127.35, 127.99, 128.55, 132.20, 136.27, 139.89, 148.12.

$^{31}$P (121.5 MHz, CDCl$_3$, 297K) δ: 23.06.

ESI MS (MeOH) calcd for C$_{24}$H$_{34}$N$_2$O$_7$P$_2$ 524.50, found m/z (M$^+$+1) 525. Hz), 122.74, 134.37, 142.91, 151.63, 154.77.

$^{19}$F NMR (282.2 MHz, CDCl$_3$, 297K) δ: −140.77.

$^{31}$P (121.5 MHz, CDCl$_3$, 297K) δ 22.79.

ESI MS (MeOH) calcd for C$_{17}$H$_{27}$FN$_2$O$_6$P$_2$ 436.36, found m/z (M$^+$+1) 437.

Example 22

2-(8-(benzyloxy)imidazo[1,2-α]pyridin-3-yl)-1-ethane-bisphosphonic acid (36)

The full synthesis of 2-(8-(benzyloxy)imidazo[1,2-α]pyridin-3-yl)-1-ethane-bisphosphonic acid (36) is schematically shown in FIG. 6. To a stirred solution of [2-(8-Benzyloxy-imidazo[1,2-α]pyridin-3-yl)-1-(diethoxy-phosphoryl)-ethyl]-phosphonic acid diethyl ester 35 (Example 21) (1.0 g, 1.9 mmol) in dry CH$_2$Cl$_2$ (10 mL) under argon was added bromotrimethylsilane (2.9 mL, 22.8 mol) and the mixture stirred at room temperature for 24 hours. The reaction mixture was concentrated in vacuo and the residue dissolved in CH$_2$Cl$_2$ (10 mL) then H$_2$O (8.0 mL) was added. The aqueous layer was separated and purified on HPLC to afford [2-(8-Benzyloxy-imidazo[1,2-α]pyridin-3-yl)-1-(diethoxy-phosphoryl)-ethy]-bisphosphonic acid 36 as pale yellow solid with a yield of 470 mg, 60%.

$^1$H NMR (300 MHz, D$_2$O+1 drop KOD, 297K) δ 2.15 (tt, J=7.5, 22.4 Hz, 1H, CH), 3.25 (dt, J=9.6, 19.5 Hz, 2H, CH$_2$), 5.27 (s, 2H, CH$_2$) 6.69 (d, J=7.5 Hz, 1H), 6.80 (t, J=7.5 Hz, 1H), 7.40 (m, 6H), 8.08 (d, J=6.9 Hz, 1H).

$^{13}$C NMR (75.5 MHz, D$_2$O+1 drop KOD, 297K) δ 23.16, 38.97 (t, 118.3 Hz), 70.18, 103.68, 112.05, 118.31, 127.63, 128.29, 128.55, 128.66, 128.73, 128.81, 136.28, 139.08, 148.12.

$^{31}$P (121.5 MHz, D$_2$O+1 drop KOD, 297K) δ 20.00.

ESI MS (D$_2$O) calcd for C$_{16}$H$_{18}$N$_2$O$_7$P$_2$ 412.28, found m/z (M$^+$+1) 413.

Example 23

[2-(8-hydroxy-imidazo[1,2-α]pyridin-3-yl)-1-(diethoxy-phosphoryl)-ethyl]-phosphonic acid diethyl ester (39)

Figure 7:
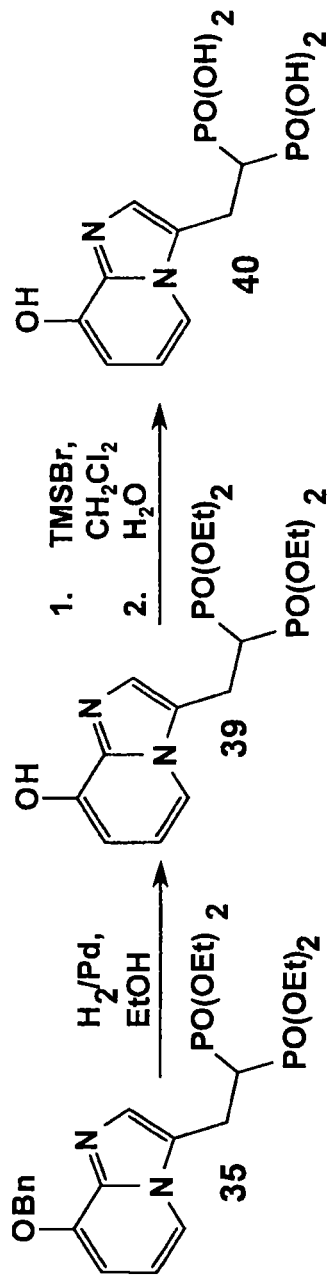
FIG. 7 schematically illustrates a process for making [2-(8-hydroxy-imidazo[1,2-α]pyridin-3-yl)-1-ethane]-bisphosphonic acid (40).

As shown in FIG. 7, [2-(8-Benzyloxy-imidazo[1,2-α]pyridin-3-yl)-1-(diethoxy-phosphoryl)-ethyl]-phosphonic acid diethyl ester 35 (Example 21) (1.5 g, 2.86 mmol) and ethanol (30 mL) were mixed in a 250-mL round bottomed flask and purged with nitrogen for 5 minutes. Palladium on carbon (10%, 50% wet, 1.5 g) was then added and the system purged for another 10 minutes. A balloon was then filled with hydrogen and attached to the reaction flask and the reaction allowed to proceed for 12 hours. The reaction mixture was then filtered through celite and concentrated under reduced pressure to afford 39. 860 mg, 72% yield. Dark yellow oil.

$^1$H NMR (300 MHz, CDCl$_3$, 297K) δ: 1.27 (m, 12H, OCH$_2$CH$_3$), 2.63 (tt, J=6.6, 23.4 Hz, 1H, PCHP), 3.54 (dt, J=9.6, 15.3 Hz, 2H, PCHCH$_2$), 4.15 (m, 8H, OCH$_2$CH$_3$), 6.96 (d, J=4.5 Hz, 1H), 7.04 (t, J=7.05 Hz, 1H), 7.71 (s, 1H), 7.89 (d, J=6.9 Hz, 1H).

$^{31}$P (121.5 MHz, CDCl$_3$, 297K) δ: 22.42.

ESI MS (MeOH) calcd for C$_{17}$H$_{28}$N$_2$O$_7$P$_2$ 434.37, found m/z (M$^+$+1) 435.

Example 24

[2-(8-hydroxy-imidazo[1,2-α]pyridin-3-yl)-1-ethane]-bisphosphonic acid (40)

The synthesis of [2-(8-hydroxy-imidazo[1,2-α]pyridin-3-yl)-1-ethane]-bisphosphonic acid (40) is illustrated schematically in FIG. 7. To a stirred solution of 39 (860 mg, 2 mmol) in dry CH$_2$Cl$_2$ (10 mL) under argon was added bromotrimethylsilane (3.1 mL, 24.0 mol) and the mixture stirred at room temperature for 24 hours. The reaction mixture was concentrated in vacuo and the residue dissolved in CH$_2$Cl$_2$ (10 mL) then H$_2$O (8.0 mL) was added. The aqueous layer was separated and purified on HPLC to afford [2-(8-hydroxy-imidazo[1,2-α]pyridin-3-yl)-1-(diethoxy-phosphoryl)-ethyl]-bisphosphonic acid 40. 300 mg, 47% yield. Pale yellow solid.

$^1$H NMR (300 MHz, D$_2$O+1 drop KOD, 297K) δ 2.05 (tt, J=4.2, 17.4 Hz, 1H, CH), 3.04 (dt, J=6.5, 11.1 Hz, 2H, CH$_2$), 6.07 (d, J=7.8 Hz, 1H), 6.60 (t, J=6.9 Hz, 1H), 7.14 (s, 1H), 7.50 (d, J=6.3 Hz, 1H).

$^{31}$P (121.5 MHz, D$_2$O+1 drop KOD, 297K) δ 20.30.

ESI MS (D$_2$O) calcd for C$_9$H$_{12}$N$_2$O$_7$P$_2$ 322.15, found m/z (M$^+$−1) 321.

Example 25

2-ethyl-imidazo[1,2-α]pyridine (70)

Figure 8:
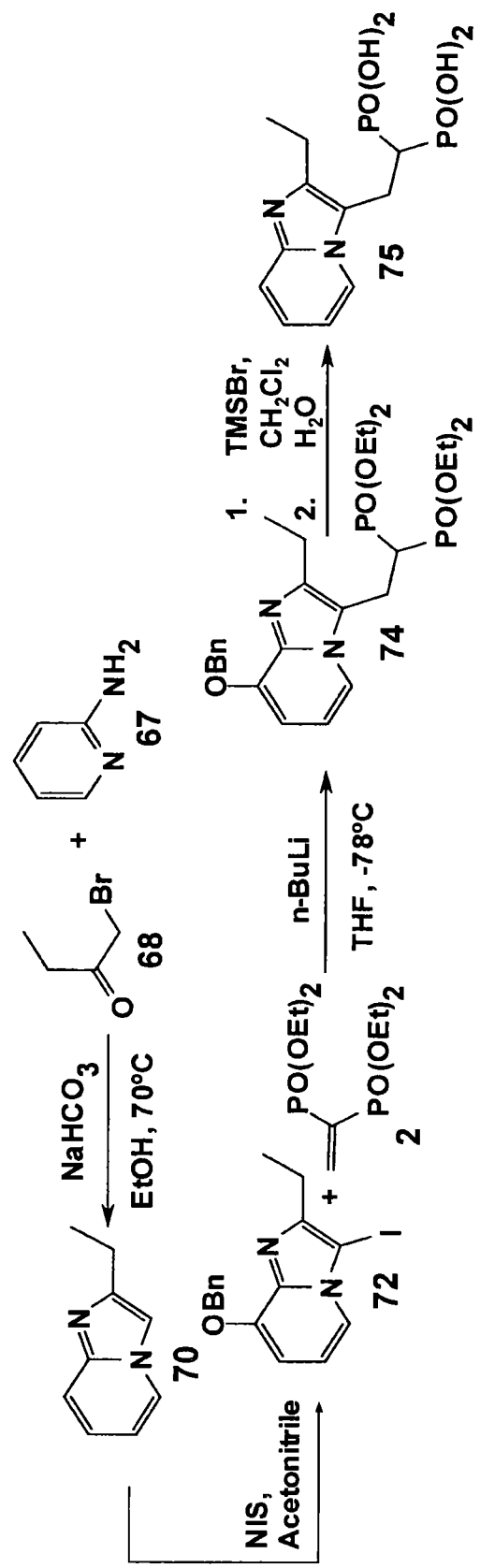
FIG. 8 schematically illustrates a process for making [(2-ethyl-imidazo[1,2-α]pyridin-3-yl)-methyl]-bisphosphonic acid (75).
Figure 9:
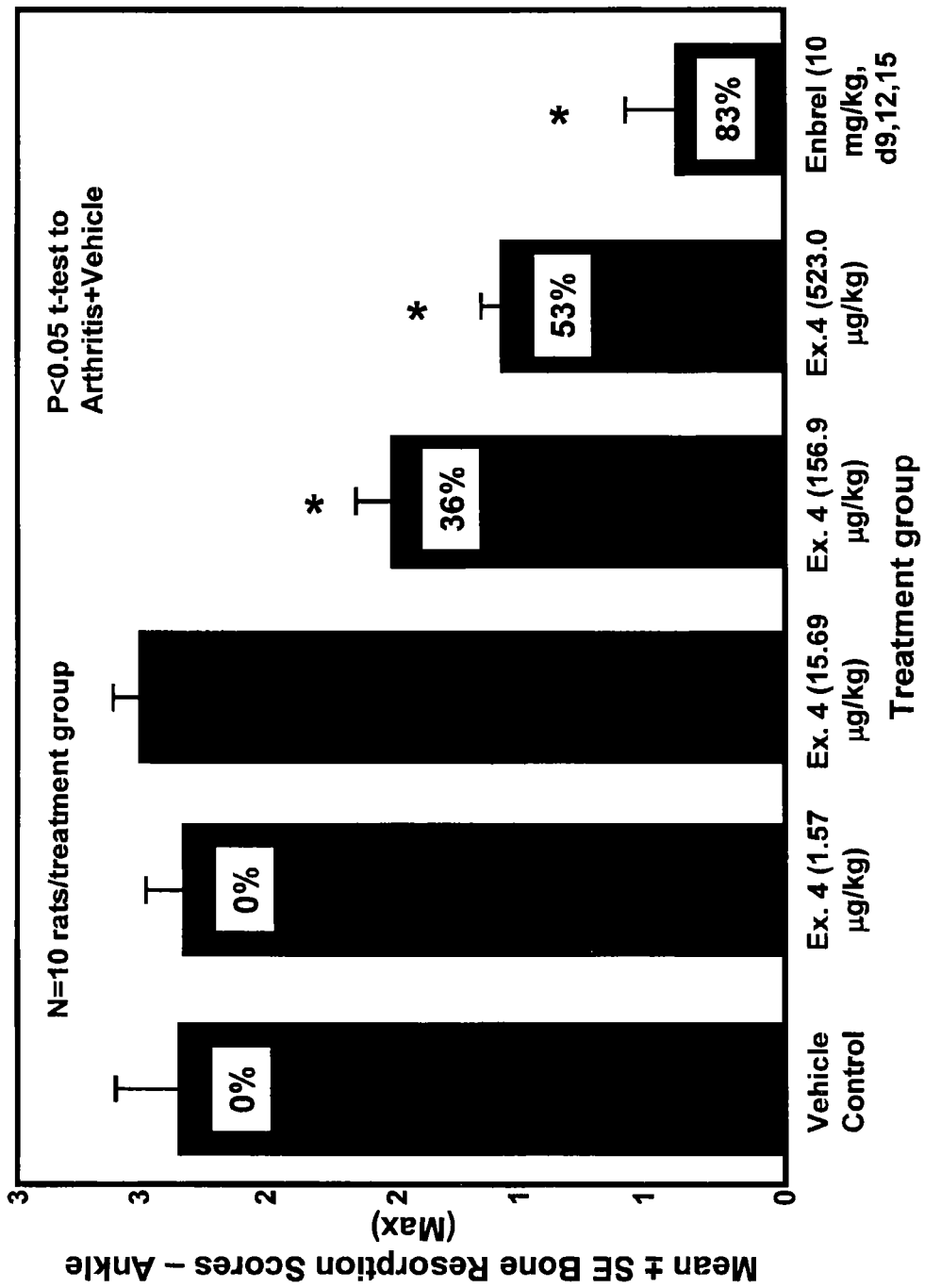
FIG. 9 is a graph showing the results of ankle bone resorption scores. There was a dose-dependent decrease in bone resorption at the ankle. The decrease was statistically different ($p=0.05$) relative to vehicle at the two highest dosage levels (156.9 µg/kg and 523.0 µg/kg).
Figure 10:
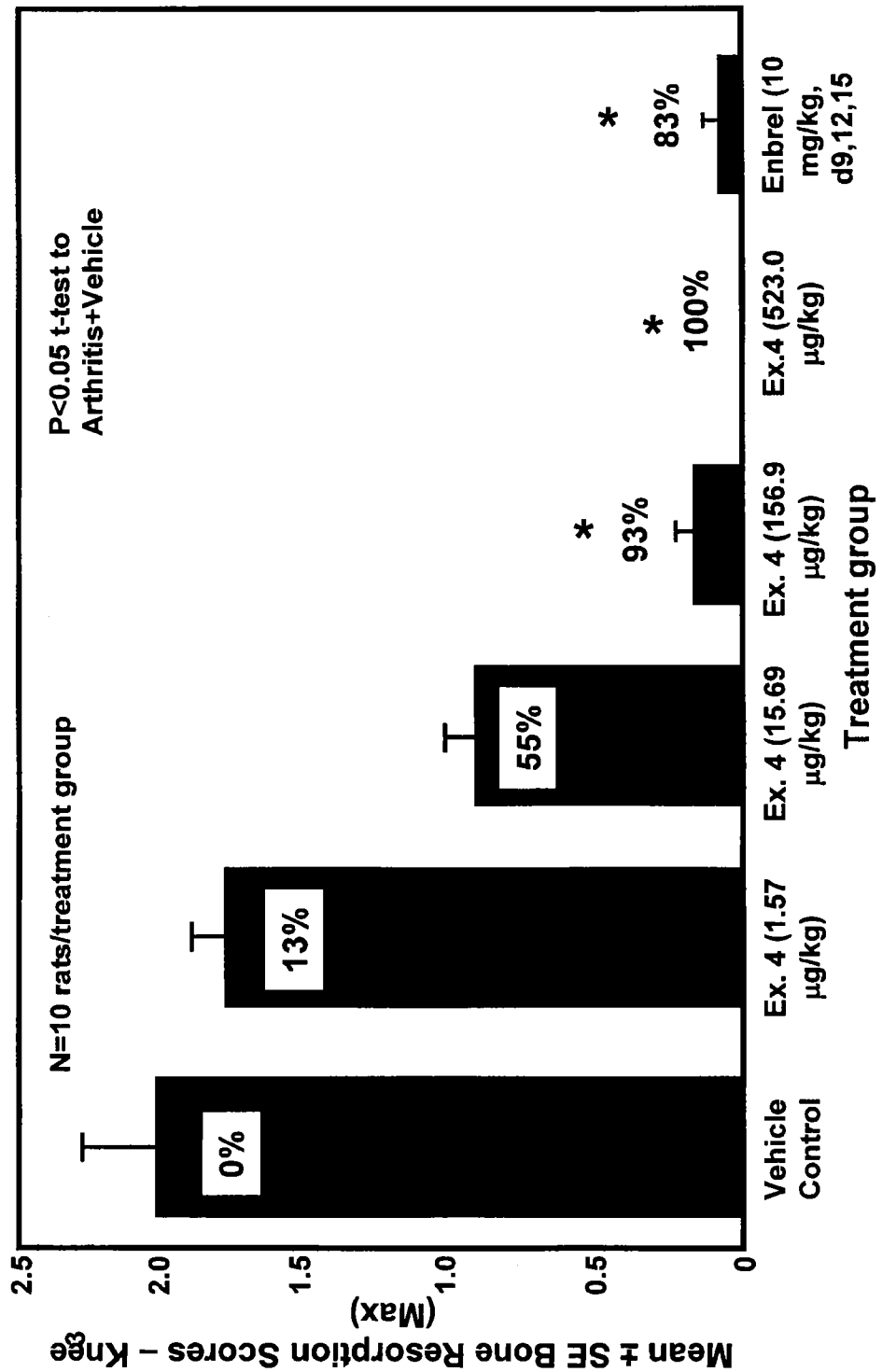
FIG. 10 is a graph showing the results of knee bone resorption scores. There was a dose dependent decrease in bone resorption. The decrease was statistically different ($p=0.05$) relative to vehicle at the three highest dosage levels (15.69 µg/kg, 156.9 µg/kg and 523.0 µg/kg).

As shown in FIG. 8, 1-Bromo-2-butanone 68 (15.0 g, 99.33 mmol) and ethanol (100 mL) were added into a 500 mL three neck round bottomed flask and stirred vigorously. 2-aminopyridine 67 (7.19 g, 76.41 mmol) was then added portion wise followed by the addition of NaHCO$_3$ (32.1 g, 382 mmol). There was evolution of gas. After the bubbling had ceased, the mixture was refluxed at 70° C. for 1.5 hours. The product and starting material had the same R$_f$ on TLC, but the product glowed. The reaction mixture was then cooled to room temperature, filtered and concentrated under reduced pressure. Methylene chloride was added to the residue at 0° C. and 10% NaOH added until the pH was 10. The mixture was then diluted with water (100 mL) and the organic phase separated, dried (Na$_2$SO$_4$) and concentrated under reduced pressure. Purification on Silica gel (CombiFlash, heptane/EtOAc elution) afforded 2-ethyl-imidazo[1,2-α]pyridine 70 as dark brown oil. 8.37 g, 75%, yield.

$^1$H NMR (400 MHz, CDCl$_3$, 297K) δ 1.26 (t, 3H, CH$_2$CH$_3$) 2.73 (q, 2H, CH$_2$CH$_3$), 6.62 (t, J=6.8 Hz, 1H), 7.02 (m, 1H), 7.25 (s, 1H), 7.43 (d, J=10 Hz, 1H) 7.95 (d, J=6.4 Hz, 1H).

ESI MS (MeOH) calcd for C$_9$H$_{10}$N$_2$ 146.19, found m/z (M$^+$+1) 147.

Example 26

2-ethyl-3-iodo-imidazo[1,2-α]pyridine (72)

As shown in FIG. 8, N-iodosuccinimide (8.37 g, 57.25 mmol) was added to a solution of 2-ethyl-imidazo[1,2-α]pyridine 70 (Example 27) (12.88 g, 57.25 mmol) in dry acetonitrile (100 mL) at 0° C. The reaction was warmed to room temperature and then stirred for 12 hours. The mixture was then concentrated and purified on silica gel (CombiFlash, Heptane/EtOAc elution) to afford 2-ethyl-3-iodo-imidazo[1,2-α]pyridine 72, as photosensitive yellow crystals with a yield of 5.6 g, 35%.

$^1$H NMR (400 MHz, CDCl$_3$, 297K) δ 1.27 (t, 3H, CH$_2$CH$_3$) 2.75 (q, 2H, CH$_2$CH$_3$), 6.79 (t, J =6.7 Hz, 1H), 7.12 (m, 1H), 7.44 (d, J=8.3 Hz, 1H) 8.01 (d, J=6.7 Hz, 1H).

ESI MS (MeOH) calcd for C$_9$H$_9$IN$_2$ 272.09, found m/z (M$^+$+1) 273.

Example 27

[(Diethoxy-phosphoryl)-(2-ethyl-imidazo[1,2-α]pyridin-3-yl)-methyl]-phosphonic acid diethyl ester (74)

As shown in FIG. 8, 2-Ethyl-3-iodo-imidazo[1,2-α]pyridine 72 (Example 28) (5.0 g, 18.34 mmol) in anhydrous THF (80 mL) was stirred at −78° C., under argon, then n-BuLi (2.5 M, 14.7 mL, 36.76 mmol) in hexanes was added slowly, keeping the temperature below −70° C. The resulting mixture was stirred for 10 minutes, then tetraethyl ethene-1,1-bisphosphonate 3 (5.52 g, 18.38 mmol) in anhydrous THF (20 mL) was added slowly, keeping the temperature below −70° C. The reaction mixture was stirred for an additional 10 min, cooled to room temperature, then quenched with saturated NH$_4$Cl (100 mL). The mixture was then extracted with CH$_2$Cl$_2$ (200 mL×3) and the organic phase washed with water (200 mL×2). The resultant organic phase was then dried (NaSO$_4$), concentrated under reduced pressure and purified on silica gel (CombiFlash, EtOAc/MeOH elution) and HPLC to afford [(diethoxy-phosphoryl)-(2-ethyl-imidazo[1,2-α]pyridin-3-yl)-methyl]-phosphonic acid diethyl ester 74 as pale yellow oil with a yield of 900 mg, 11%.

$^1$H NMR (400 MHz, CDCl$_3$, 297K) δ 1.19 (m, 12H, OCH$_2$CH$_3$), 1.32 (t, 3H, CH$_2$CH$_3$) 2.84 (tt, J=5.5, 16.9 Hz, 1H, PCHP), 2.88 (q, 2H, CH$_2$CH$_3$), 3.57 (dt, J=8.5, 15.8 Hz, 2H, CH$_2$), 4.10 (m, 8H), 7.32 (t, J=6.8 Hz, 1 H), 7.71 (t, J=7.6 Hz, 1H), 7.97 (d, J=9.2 Hz, 1H), 8.47 (d, J=6.8 Hz, 1H).

$^{31}$P (162 MHz, CDCl$_3$, 297K) δ: 20.67.

ESI MS (MeOH) calcd for C$_{19}$H$_{32}$N$_2$O$_6$P$_2$ 446.42, found m/z (M$^+$+1) 447.

Example 28

[(2-ethyl-imidazo[1,2-α]pyridin-3-yl)-methyl]-bis-phosphonic acid (75)

The synthesis of [(2-ethyl-imidazo[1,2-α]pyridin-3-yl)methyl]-bisphosphonic acid (75) is schematically illustrated in FIG. 8. [(Diethoxy-phosphoryl)-(2-ethyl-imidazo[1,2-α]pyridin-3-yl)-methyl]-phosphonic acid diethyl ester 74 (Example 29) (860 mg, 1.93 mmol) was dissolved in anhydrous dichloromethane (20 mL) and TMSBr (2.5 mL, 19.3 mmol) added and the mixture stirred at room temperature for 48 hours. The reaction was then stopped and the excess TMSBr removed under reduced pressure, then the residue dissolved in dichloromethane (20 mL) and water (10 mL) added. The mixture was stirred for 30 seconds then the aqueous layer was separated, filtered and purified on HPLC. The pure fractions were combined, the volume reduced under reduced pressure and the resultant aqueous solution lyophilized to afford [(Diethoxy-phosphoryl)-(2-ethyl-imidazo[1,2-α]pyridin-3-yl)-methyl]-bisphosphonic 75. 370 mg, 57% yield. Colorless solid.

$^1$H NMR (400 MHz, D$_2$O+1 drop KOD) δ 1.19 (t, 3H), 2.05 (tt, J=6.0, 15.2 Hz, 1H, CH), 2.80 (q, 2H), 3.33 (dt, J=7.6, 14.4 Hz, 2H, CH$_2$), 6.86 (t, J=6.8 Hz, 1H), 7.20 (t, J =8.8 Hz, 1H), 7.35 (d, J=9.2 Hz, 1H), 8.61 (d, J=6.8 Hz, 1H).

$^{31}$P (162 MHz, D$_2$O+1 drop KOD, 297K) δ 21.35.

ESI MS (D$_2$O) calcd for C$_{11}$H$_{16}$N$_2$O$_6$P$_2$ 334.21, found m/z (M$^+$−1) 333.

Example 29

Hydroxyapatite (HAP) Affinity

Mineral affinity for hydroxyapatite was evaluated by chromatographic profiling of the novel bisphosphonate compounds. Hydroxyapatite (HAP) ceramic spheres (20 mm diameter, BioRad) were packed in a 0.66×6.5 cm glass column (Omnifit®). The HAP columns were attached to a Waters 650E Advanced Protein Purification System (FPLC) (Millipore) in a running buffer of 1 mM KPO$_3$ at pH 6.8. Each compound was prepared in 1 mM KPO$_3$ buffer at pH6.8 and 400 μmoles were injected into the FPLC system. The bisphosphonate compounds were eluted in a gradient of phosphate buffer, concentration increasing from 1 mM up to 1000 mM and detected by a Waters 484 UV absorbance detector (Millipore) at their optimum wavelength. Table 1 shows the HAP retention profiles of each compound (determined in triplicate for statistical analyses). Longer retention times (minutes) correspond with higher affinity to the HAP sphere and, correspondingly, higher mineral affinity.

TABLE 1

HAP Affinity

| Example | Retention time (min) |
| --- | --- |
| 1-fluoro-2-(imidazo-[1,2-α]pyridin-3-yl)-ethyl-bisphosphonic acid (23) | 6.17 |
| 2-(Imidazo-[1,2-α]pyridin-3-yl)-ethyl-bisphosphonic acid (80) | 6.6 |
| [(2-ethyl-imidazo[1,2-α]pyridin-3-yl)-methyl]-bisphosphonic acid (75) | 4.83 |
| 2-(7-methyl)-imidazo-[1,2-α]pyridin-3-yl-ethyl-bisphosphonic acid (15) | 6.6 |
| 1-fluoro-2-(7-methyl)-imidazo-[1,2-α]pyridin-3-yl-ethyl-bisphosphonic acid (11) | 6.2 |
| [2-(6-Fluoro-imidazo[1,2-α]pyridin-3-yl)-ethyl]-bisphosphonic acid (34) | 6.3 |
| 2-(6-Methylimidazo-[1,2-α]Pyridin-3-yl)-Ethyl-Bisphosphonic Acid (81) | 6.6 |
| [2-(8-hydroxy-imidazo[1,2-α]pyridin-3-yl)-1-ethane]-bisphosphonic acid (40) | 5.3 |
| Minodronate | 10.33 |
| Risedronate | 9.97 |
| Alendronate | 17.5 |
| Zoledronate | 12.53 |

Example 30

FPPS Inhibition

The compounds were evaluated for in vitro inhibition of human farnesyl pyrophosphate synthase (FPPS), the major molecular target of nitrogen-containing bisphosphonate compounds. Inhibition of FPPS correlates with inhibition of bone resorption in vivo. Accordingly, FPPS inhibition is an indicator of the potency of the bisphosphonate compounds. The general principles of this method are disclosed in Dunford et al., *J. Med. Chem.*, 51: 2187-2195 (2008) and Dunford et al., *J. Pharmacol. Exp. Ther.*, 296: 235-242 (2001), the disclosures of which are incorporated herein by reference in their entireties.

Recombinant human FPPS was expressed and purified as described in Dunford et al., *J. Med. Chem.,* 51: 2187-2195 (2008). For kinetic analysis, 40 ng (1 pmol) of pure FPP synthase were assayed in a final volume of 100 µL buffer containing 50 mM Tris pH 7.7, 2 mM MgCl2, 0.5 mM TCEP and 20 µg/mL BSA. The concentrations of substrates, GPP and IPP (14C-IPP, 400 KBq/µmol) were 10 µM each in the standard reaction. Reactions also contained the appropriate concentration of the appropriate bisphosphonate compound. Reactions were started with the addition of enzyme at 2 µg/mL in enzyme dilution buffer (10 mM HEPES pH 7.5, 500 mM NaCl, 5% glycerol, 2 mM TCEP, 20 µg/mL BSA) and allowed to proceed for an appropriate period of time at 37° C. The reaction mixtures were then extracted with 0.4 mL of ligroin to separate reaction products from unused substrate and, after thorough mixing, 0.2 mL of the ligroin upper phase was combined with 4 mL of general purpose scintillant.

The final inhibition constant ($K_i$) and $IC_{50}$ value, shown in Table 2, were calculated as described in the literature. These data demonstrate the enzyme inhibitory activity of the bisphosphonate compounds described herein is consistent with the inhibitory activity of known effective bisphosphonate compounds, despite the reduced affinity for bone mineral.

TABLE 2

FPPS inhibition

| Example | $IC_{50}$ nM[1] | $K_i$ |
|---|---|---|
| 1-fluoro-2-(imidazo-[1,2-α]pyridin-3-yl)-ethyl-bisphosphonic acid (23) | 2.46 | 0.014 |
| 2-(Imidazo-[1,2-α]pyridin-3-yl)-ethyl-bisphosphonic acid (80) | 2.59 | 0.013 |
| [(2-ethyl-imidazo[1,2-α]pyridin-3-yl)-methyl]-bisphosphonic acid (75) | 27 | 2.5 |
| 2-(7-methyl)-imidazo-[1,2-α]pyridin-3-yl-ethyl-bisphosphonic acid (15) | 39.7 | 6.1 |
| 1-fluoro-2-(7-methyl)-imidazo-[1,2-α]pyridin-3-yl-ethyl-bisphosphonic acid (11) | 60.3 | 9.6 |
| [2-(6-Fluoro-imidazo[1,2-α]pyridin-3-yl)-ethyl]-bisphosphonic acid (34) | 106.4 | 17.5 |
| 2-(6-Methylimidazo-[1,2-α]Pyridin-3-yl)-Ethyl-Bisphosphonic Acid (81) | 380 | 64 |
| [2-(8-hydroxy-imidazo[1,2-α]pyridin-3-yl)-1-ethane]-bisphosphonic acid (40) | 893 | 151 |
| Minodronate | 1.9 | 0.0005 |
| Risedronate | 5.7 | 0.36 |
| Alendronate | 330.4 | 57 |
| Zoledronate | 4.1 | 0.07 |

[1]After pre-incubation

Example 31

Schenk Model

The compounds were evaluated for in vivo bone resorption inhibition and mineralization inhibition in an animal model system known in the field of bone metabolism as the Schenk Model. The general principles of this model system are disclosed in Shinoda et al., *Calcif. Tissue Int.,* 35: 87-99 (1983); and in Schenk et al., *Calcif. Tissue Res.* 11: 196-214 (1973), the disclosures of which are incorporated herein by reference in their entireties.

Animals: Weanling male Sprague Dawley rats (Charles River Breeding Laboratories, Raleigh, N.C.) approximately 6 weeks old with weights ranging between 120 and 150 grams were placed into groups based on body weight, with 6 animals per group. All groups received treatment by subcutaneous injection (SQ) once daily (QD) for 7 days.

Dose Solutions and Dosing Procedure: On day 0, all animals received an injection of 3% xylenol orange (90 mg/kg; Sigma) in normal saline, pH adjusted to 7.4. On day 4 all animals were given a subcutaneous injection of 1% Calcein (10 mg/kg, Sigma) in 0.9% NaCl solution to label the skeleton. The first treatment was on day 0, and the last treatment on day 6, with animals euthanized on day 7. Concentrations were based on dosing 0.2 ml/100 g body weight. Compounds were administered at doses ranging from 0.0001 to 1 mg P/kg/day for 7 days at semi-log doses. The dose range was based on the IC 50 in the FPPS inhibition assay, and on the affinity to hydroxyapatite (HAP Affinity). Three to seven doses were chosen per test compound. Adjustments in dosage based on changes in body weight were made on a daily basis.

Necropsy, Tissue Processing and Histomorphometry: On day 7 after the start of dosing, all animals were euthanized via exsanguination under gas anesthesia and/or $CO_2$. The right tibia and femur were dissected free and placed in 70% ethyl alcohol. The proximal metaphysis of the right tibia was analyzed using dual energy x-ray analysis (DXA). This provides information on changes in both cortical and cancellous bone density. The primary end-point for this study was bone mineral density in the tibia measured using a Hologics QDR-4500 densitometer (Hologics, Inc). Statistical evaluation of data was made using parametric and non-parametric analysis of variance and Wilcoxon's rank sum test to determine a statistically significant effect compared to control animals.

The Schenk model provided data for in vivo bone resorption inhibition by the compounds, see Table 3. Bone mineral density (BMD) was assessed with a Hologics 4500A on a region of the proximal tibial metaphysic. Efficacy of each bisphosphonate was expressed as the percent change from the vehicle control group. The dose that increased bone mineral density (BMD) 20% greater than control was determined via a logistic dose response relationship (SAS), which estimates an efficacy value using all animals in the study, and identified as D20 for comparison of bisphosphonates across studies. (Lundy et al., *J. Bone Min. Res.* 22(Suppl 1): S443, (2007)). Data from compounds run in multiple studies was averaged.

TABLE 3

Schenk Model

| Example | Schenk D20 (mg P/kg) 20% > BMD than control |
|---|---|
| 1-fluoro-2-(imidazo-[1,2-α]pyridin-3-yl)-ethyl-bisphosphonic acid (23) | 0.0003 |
| 2-(Imidazo-[1,2-α]pyridin-3-yl)-ethyl-bisphosphonic acid (80) | 0.0006 |
| 2-(7-methyl)-imidazo-[1,2-α]pyridin-3-yl-ethyl-bisphosphonic acid (15) | 0.008 |
| 1-fluoro-2-(7-methyl)-imidazo-[1,2-α]pyridin-3-yl-ethyl-bisphosphonic acid (11) | 0.002 |
| Minodronate | 0.0001 |
| Risedronate | 0.00045 |
| Alendronate | 0.0015 |
| Zoledronate | 0.00008 |

Example 34

CIA Rat Model

The collagen induced arthritis (CIA) rat model is an in vivo model that provides for an evaluation of the inhibition of inflammation as well as inhibition of bone erosion. The study was performed according to the method of Bendele et al., *Arthritis & Rheumatism,* 43: 2648-2659 (2000), incorporated herein by reference in its entirety, with the exception that male animals were used instead of female animals.

Arthritis was induced in rats by injecting collagen on days 0 and 6. The bisphosphonate compound of Example 4 (1-fluoro-2-(imidazo-[1,2-α]pyridin-3-yl)-ethyl-bisphosphonic acid) was administered at four different dosages (1.57 μg/kg, 15.69 μg/kg, 156.9 μg/kg, and 523.0 μg/kg; n=10/group) by subcutaneous injection on day 0, and compared to vehicle control (n=10). An additional group was administered 10 mg/kg Enbrel® (n=10) on days 9, 12, and 15 as a positive control. The study was stopped on day 17 and the animals were evaluated for ankle thickness and paw weight, indices of inflammation. The ankle and knees were removed as one piece, placed in formalin, decalcified and processed for histology. Sections were stained with toluidine blue and graded for inflammation, pannus and cartilage degradation on a score of 0 (normal) to 5 (severe). Bone erosion was also scored in the ankle and knee on a 0-5 score.

When ranges are used herein for physical properties, such as molecular weight, or chemical properties, such as chemical formulae, all combination and sub-combinations of ranges of specific embodiments therein are intended to be included.

We claim:

1. A compound, or a pharmaceutically acceptable salt thereof, wherein the compound has a structure according to Formula I

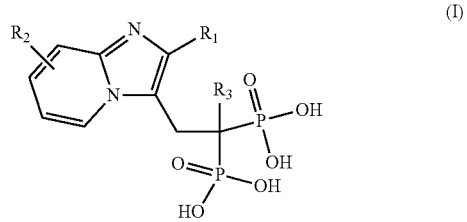

(I)

wherein:
R$_1$ is hydrogen, hydroxyl, lower alkyl, methoxy, or F;
R$_2$ is hydrogen, hydroxyl, lower alkyl, or F; and
R$_3$ is F, Cl, or hydrogen.

2. The compound of claim 1, wherein R$_1$ and R$_2$ are each independently hydrogen, hydroxyl, methyl, ethyl, t-butyl, or F.

3. The compound of claim 1, wherein R$_1$ is hydrogen or a lower alkyl, and R$_2$ is hydrogen, hydroxyl, methyl, or F.

4. The compound of claim 1, wherein R$_1$ is hydrogen, ethyl, or t-butyl, and R$_2$ is hydrogen, hydroxyl, methyl, or F.

5. The compound of claim 1, wherein R$_3$ is hydrogen or F.

6. The compound of claim 1, wherein R$_1$ is hydrogen, R$_2$ is hydrogen or methyl, and R$_3$ is hydrogen or F.

7. The compound of claim 1, wherein R$_1$ is ethyl or t-butyl, R$_2$ is hydrogen, and R$_3$ is hydrogen or F.

8. The compound of claim 1, wherein the compound is selected from the group consisting of: 1-fluoro-2-(imidazo[1,2-α]pyridin-3-yl-ethyl-bisphosphonic acid; 2-(imidazo[1,2-α]pyridin-3-yl)-ethyl-bisphosphonic acid; 2-(6-methylimidazo[1,2-α]pyridin-3-yl) -ethyl-bisphosphonic acid; [(2-ethyl-imidazo[1,2-α]pyridin-3-yl)-methyl]-bisphosphonic acid; 2-(2-t-butylimidazo[1,2-α]pyridin-3-yl)ethane-1,1-bisphosphonic acid; 2-(7-methylimidazo[1,2-α]pyridin-3-yl)ethyl-bisphosphonic acid; [2-(8-hydroxy-imidazo [1,2-α]pyridin-3-yl)-1-ethane]-bisphosphonic acid; 2-(6-fluoroimidazo[1,2-α]pyridin-3-yl)-ethyl-bisphosphonic acid; and 1-fluoro-2-(7-methylimidazo[1,2-α]pyridin-3-yl)-ethyl-bisphosphonic acid, or a pharmaceutically acceptable salt thereof.

9. The compound of claim 1, wherein the compound is 1-fluoro-2-(imidazo[1,2-α]pyridin-3-yl)-ethyl-bisphosphonic acid.

10. A pharmaceutical composition comprising:
a compound, or a pharmaceutically acceptable salt thereof, wherein the compound has a structure according to Formula I

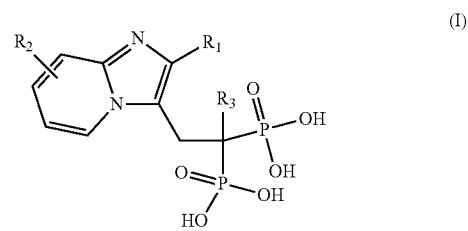

(I)

wherein:
R$_1$ is hydrogen, hydroxyl, lower alkyl, methoxy, or F;
R$_2$ is hydrogen, hydroxyl, lower alkyl, or F; and
R$_3$ is F, Cl, or hydrogen; and
a pharmaceutically acceptable carrier.

11. The composition of claim 10, wherein R$_1$ and R$_2$ are each independently hydrogen, hydroxyl, methyl, ethyl, t-butyl, or F.

12. The composition of claim 10, wherein R$_3$ is hydrogen or F.

13. The composition of claim 10, wherein R$_1$ is hydrogen; R$_2$ is hydrogen or methyl; and R$_3$ is hydrogen or F.

14. The composition of claim 10, wherein R$_1$ is ethyl or t-butyl; R$_2$ is hydrogen; and R$_3$ is hydrogen or F.

15. The composition of claim 10, wherein the compound is selected from the group consisting of: 1-fluoro-2-(imidazo[1,2-α]pyridin-3-yl-ethyl-bisphosphonic acid; 2-(imidazo[1,2-α]pyridin-3-yl)-ethyl-bisphosphonic acid; 2-(6-methylimidazo[1,2-α]pyridin-3-yl) -ethyl-bisphosphonic acid; [(2-ethyl-imidazo[1,2-α]pyridin-3-yl)-methyl]-bisphosphonic acid; 2-(2-t-butylimidazo[1,2-α]pyridin-3-yl)ethane-1,1-bisphosphonic acid; 2-(7-methylimidazo[1,2-α]pyridin-3-yl)ethyl-bisphosphonic acid; [2-(8-hydroxy-imidazo [1,2-α]pyridin-3-yl)-1-ethane]-bisphosphonic acid; 2-(6-fluoroimidazo[1,2-α]pyridin-3-yl)-ethyl-bisphosphonic acid; and 1-fluoro-2-(7-methylimidazo[1,2-α]pyridin-3-yl)-ethyl-bisphosphonic acid, or a pharmaceutically acceptable salt thereof.

16. The composition of claim 10, wherein the compound comprises 1-fluoro-2-(imidazo[1,2-α]pyridin-3-yl)ethane-1,1-diyldiphosphonic acid, or a pharmaceutically acceptable salt thereof, and a pharmaceutically acceptable carrier.

17. The composition of claim 10, wherein the compound further comprises at least one pharmaceutically active ingredient other than a bisphosphonic acid, or pharmaceutically acceptable salt thereof.

18. The composition of claim 17, wherein the at least one pharmaceutically active ingredient is selected from the group consisting of: an anti-inflammatory, an immunomodulator, a chelator, a musculoskeletal anabolic agent, and a combination thereof.

\* \* \* \* \*

UNITED STATES PATENT AND TRADEMARK OFFICE
CERTIFICATE OF CORRECTION

PATENT NO.        : 8,618,079 B2
APPLICATION NO.   : 13/120078
DATED             : December 31, 2013
INVENTOR(S)       : Ebetino et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 115 days.

Signed and Sealed this
Twenty-second Day of September, 2015

Michelle K. Lee
*Director of the United States Patent and Trademark Office*